(12) United States Patent
Hill

(10) Patent No.: US 7,084,984 B2
(45) Date of Patent: Aug. 1, 2006

(54) APPARATUS AND METHOD FOR HIGH SPEED SCAN FOR DETECTION AND MEASUREMENT OF PROPERTIES OF SUB-WAVELENGTH DEFECTS AND ARTIFACTS IN SEMICONDUCTOR AND MASK METROLOGY

(75) Inventor: Henry Allen Hill, Tucson, AZ (US)

(73) Assignee: Zetetic Institute, Tucson, AZ (US)

( * ) Notice: Subject to any disclaimer, the term of this patent is extended or adjusted under 35 U.S.C. 154(b) by 0 days.

(21) Appl. No.: 10/886,010

(22) Filed: Jul. 7, 2004

(65) Prior Publication Data

US 2005/0036149 A1    Feb. 17, 2005

Related U.S. Application Data

(60) Provisional application No. 60/485,507, filed on Jul. 7, 2003.

(51) Int. Cl.
*G01B 9/02* (2006.01)
(52) U.S. Cl. ...................................... 356/450
(58) Field of Classification Search ................ 356/450, 356/484, 489, 496, 511, 521
See application file for complete search history.

(56) References Cited

U.S. PATENT DOCUMENTS

| 3,628,027 | A | 12/1971 | Brauss |
| 3,748,015 | A | 7/1973 | Offner |
| 4,011,011 | A | 3/1977 | Hemstreet et al. |
| 4,226,501 | A | 10/1980 | Shafer |
| 4,272,684 | A | 6/1981 | Seachman |
| 4,685,803 | A | 8/1987 | Sommargren |
| 4,733,967 | A | 3/1988 | Sommargren |
| 5,220,403 | A | 6/1993 | Batchelder |
| 5,241,423 | A | 8/1993 | Chiu et al. |
| 5,327,223 | A | 7/1994 | Korth |
| 5,485,317 | A | 1/1996 | Perissinotto |
| 5,602,643 | A | 2/1997 | Barrett |

(Continued)

OTHER PUBLICATIONS

U.S. Appl. No. 09/852,369, filed Jan. 3, 2002, Hill.

(Continued)

*Primary Examiner*—Gregory J. Toatley, Jr.
*Assistant Examiner*—Michael A. Lyons
(74) *Attorney, Agent, or Firm*—Wilmer Cutler Pickering Hale and Dorr

(57) ABSTRACT

A method of detecting defects or artifacts on or in an object, wherein the defects or artifacts are characterized by a characteristic dimension, the method involving: generating an input beam for illuminating a spot at a selected location on or in the object, wherein the spot has a size L that is substantially larger than the characteristic dimension; deriving a measurement beam and a reference beam from the input beam; directing the measurement beam onto the object as an incident measurement beam that illuminates the spot at that selected location on or in the object to produce a backscattered measurement beam; interfering the backscattered measurement beam with the reference beam to produce an interference beam, the reference beam being oriented relative to the backscattered measurement beam so as to produce a peak sensitivity for a portion of the backscattered measurement beam that emanates from the object at a predetermined diffraction angle; converting the interference beam for that selected location into an interference signal; and using the interference signal for that selected location to determine whether any defects or artifacts characterized by said characteristic dimension are present anywhere within a region on or in the object defined by the spot at that selected location.

21 Claims, 11 Drawing Sheets

U.S. PATENT DOCUMENTS

| | | | |
|---|---|---|---|
| 5,614,763 A | 3/1997 | Womack | |
| 5,633,972 A | 5/1997 | Walt | |
| 5,659,420 A | 8/1997 | Wakai | |
| 5,699,201 A | 12/1997 | Lee | |
| 5,757,493 A | 5/1998 | Vankerkhove | |
| 5,760,901 A | 6/1998 | Hill | |
| 5,828,455 A | 10/1998 | Smith | |
| 5,894,195 A | 4/1999 | McDermott | |
| 5,915,048 A | 6/1999 | Hill et al. | |
| 5,923,423 A * | 7/1999 | Sawatari et al. | 356/484 |
| 6,011,654 A | 1/2000 | Schweizer et al. | |
| 6,018,391 A * | 1/2000 | Yoshida | 356/484 |
| 6,052,231 A | 4/2000 | Rosenbluth | |
| 6,091,496 A | 7/2000 | Hill | |
| 6,124,931 A | 9/2000 | Hill | |
| 6,271,923 B1 | 8/2001 | Hill | |
| 6,330,065 B1 | 10/2001 | Hill | |
| 6,445,453 B1 | 9/2002 | Hill | |
| 6,447,122 B1 | 9/2002 | Kobayashi et al. | |
| 6,480,285 B1 | 11/2002 | Hill | |
| 6,552,805 B1 | 4/2003 | Hill | |
| 6,552,852 B1 | 4/2003 | Hill | |
| 6,597,721 B1 | 7/2003 | Hutchinson et al. | |
| 6,606,159 B1 | 8/2003 | Hill | |
| 6,667,809 B1 | 12/2003 | Hill | |
| 6,714,349 B1 | 3/2004 | Nam | |
| 6,717,736 B1 | 4/2004 | Hill | |
| 6,753,968 B1 | 6/2004 | Hill | |
| 6,775,009 B1 | 8/2004 | Hill | |
| 6,806,959 B1 * | 10/2004 | Tukker | 356/484 |
| 6,847,029 B1 | 1/2005 | Hill | |
| 6,847,452 B1 | 1/2005 | Hill | |
| 2002/0074493 A1 | 6/2002 | Hill | |
| 2002/0131179 A1 | 9/2002 | Hill | |
| 2003/0174992 A1 | 9/2003 | Levene | |
| 2004/0201853 A1 | 2/2004 | Hill | |
| 2004/0201852 A1 | 10/2004 | Hill | |
| 2004/0201854 A1 | 10/2004 | Hill | |
| 2004/0201855 A1 | 10/2004 | Hill | |
| 2004/0202426 A1 | 10/2004 | Hill | |
| 2004/0227950 A1 | 11/2004 | Hill | |
| 2004/0227951 A1 | 11/2004 | Hill | |
| 2004/0228008 A1 | 11/2004 | Hill | |
| 2004/0246486 A1 | 12/2004 | Hill | |
| 2004/0257577 A1 | 12/2004 | Hill | |
| 2005/0036149 A1 | 2/2005 | Hill | |

OTHER PUBLICATIONS

U.S. Appl. No. 09/917,402, filed Jul. 27, 2001, Hill.
U.S. Appl. No. 10/765,254, filed Jan. 27, 2004, Hill.
U.S. Appl. No. 10/765,368, filed Jan. 27, 2004, Hill.
U.S. Appl. No. 10/886,157, filed Jul. 7, 2004, Hill.
U.S. Appl. No. 60/442,858, filed Jul. 27, 2002, Hill.
U.S. Appl. No. 60/442,982, filed Jan. 29, 2003, Hill.
U.S. Appl. No. 60/443,980, filed Jan. 31, 2003, Hill.
U.S. Appl. No. 60/444,707, filed Jan. 4, 2003, Hill.
U.S. Appl. No. 60/445,739, filed Feb. 7, 2003, Hill.
U.S. Appl. No. 60/447,254, filed Feb. 13, 2003, Hill.
U.S. Appl. No. 60/448,250, filed Jan. 19, 2003, Hill.
U.S. Appl. No. 60/448,360, filed Feb. 19, 2003, Hill.
U.S. Appl. No. 60/459,425, filed Apr. 11, 2003, Hill.
U.S. Appl. No. 60/459,493, filed Apr. 1, 2003, Hill.
U.S. Appl. No. 60/460,129, filed Apr. 3, 2003, Hill.
U.S. Appl. No. 60/485,255, filed Jul. 7, 2003, Hill.
U.S. Appl. No. 60/485,507, filed Jul. 7, 2003, Hill.
U.S. Appl. No. 60/501,666, filed Sep. 10, 2003, Hill.
U.S. Appl. No. 60/506,715, filed Sep. 26, 2003, Hill.

* cited by examiner

APPARATUS AND METHOD FOR HIGH SPEED SCAN FOR DETECTION AND MEASUREMENT OF PROPERTIES OF SUB-WAVELENGTH DEFECTS AND ARTIFACTS IN SEMICONDUCTOR AND MASK METROLOGY

This application claims the benefit of U.S. Provisional Application No. 60/485,507, filed Jul. 7, 2003.

TECHNICAL FIELD

This invention relates generally to interferometric measurement tools and methods.

BACKGROUND OF THE INVENTION

Various measurement tools have been developed that measure the intensities of scattered/reflected beams by an object so as to detect defects and/or artifacts on unpatterned and patterned wafers and lithography masks.

SUMMARY OF THE INVENTION

Some of the novel aspects of the inventions described herein include the following. One novel aspect is the practice of backscattered imaging of an object comprising the interferometric measurement of conjugated quadratures of fields of beams backscattered by an object which gives information in the form of an amplitude and an interferometric phase. Another novel aspect is the practice of backscattered imaging comprising joint measurements of conjugated quadratures of fields of backscattered beams by an object based on interferometric measurements. A further novel aspect is the practice of backscattered imaging by measuring simultaneously each component of conjugated quadratures of fields of backscattered beams by an array of a large number of spots in or on an object based on interferometric measurements. Still another novel aspect is the practice of backscattered imaging with simultaneous joint measurements of conjugated quadratures of fields of backscattered beams by a large array of spots in or on an object based on interferometric measurements.

Embodiments of the invention generate one-, two-, and three-dimensional backscattered images of an object with the measurement of conjugated quadratures of fields of backscattered beams by an object based on interferometric measurements. Certain embodiments of the invention further generate one-, two-, and three-dimensional backscattered images of an object with joint measurements of conjugated quadratures of fields of backscattered beams by an object based on interferometric measurements.

In other embodiments of the invention, backscattered images of an object are generated with simultaneous measurements made of conjugated quadratures of fields of backscattered beams by an array of a large number of spots in or on an object based on interferometric measurements but with the components of the conjugated quadratures are not measured jointly. In yet other embodiments of the invention, backscattered images of an object are generated with simultaneous joint measurements made of conjugated quadratures of fields of backscattered beams by a large array of spots in or on an object based on interferometric measurements.

In other embodiments of the invention, backscattered images of an object are generated with simultaneous measurements of conjugated quadratures of backscattered fields of polarized measurement beams with the components of the conjugated quadratures measured jointly or not measured jointly.

In some aspects, the invention teaches the measurement of the conjugated quadratures of high frequency spatial components of fields scattered by a defect or by artifacts of an object such as an unpatterned or patterned wafer or lithography mask wherein the measurement beams may comprise one or more polarization states.

In other aspects the invention further teaches the measurement of the location of defects and artifacts from the interferometric phase given by the corresponding the conjugated quadratures of high frequency spatial components of fields scattered by the defect and artifacts of an object.

In general, in one aspect, the invention features a method of detecting defects or artifacts on or in an object, therein the defects or artifacts characterized by a characteristic dimension. The method involves: generating an input beam for illuminating a spot at a selected location on or in the object, the spot having a size L that is substantially larger than the characteristic dimension; deriving a measurement beam and a reference beam from the input beam; directing the measurement beam onto the object as an incident measurement beam that illuminates said spot at that selected location on or in the object to produce a backscattered measurement beam; interfering the backscattered measurement beam with the reference beam to produce an interference beam, the reference beam being oriented relative to the backscattered measurement beam so as to produce a peak sensitivity for a portion of the backscattered measurement beam that emanates from the object at a predetermined diffraction angle; converting the interference beam for that selected location into an interference signal; and using the interference signal for that selected location to determine whether any defects or artifacts characterized by the characteristic dimension are present anywhere within a region on or in the object defined by the spot at that selected location.

Other embodiments include one ore more of the following features. The spot size L is at least three times greater than the characteristic dimension or alternatively at least an order of magnitude larger than the characteristic dimension. The incident measurement beam is at an angle of incidence $\theta_I$ with respect to a direction that is normal to the surface of the object, the predetermined diffraction angle is an angle $\theta_D$ relative to the direction that is normal to the surface of the object, the characteristic dimension is equal to $\Lambda$, the incident measurement beam is characterized by a wavelength $\lambda$, and the diffraction angle $\theta_D$ is selected to satisfy the following relationship: $\Lambda[\sin(\theta_I)-\sin(\theta_D)]=\lambda$. The method also includes performing the steps of generating, deriving, directing, interfering, and converting for each of a sequence of different selected locations on or in the object, wherein the first-mentioned selected location is one of the plurality of different selected locations. Generating the input beam involves generating a first beam at a first wavelength and a second beam at a second wavelength that is different from the first wavelength, wherein the first and second beams are coextensive and share the same temporal window. For each of a plurality of successive time intervals, introducing a corresponding different shift in a selected parameter of the first beam and introducing a different corresponding shift in the selected parameter of the second beam, wherein said selected parameters are selected from a group consisting of phase and frequency. Using the interference signal to determine whether any defects or artifacts are present involves: for each of the plurality of successive time intervals, measuring a value of the interference signal; from the measured values of the interference signal for the plurality of successive time internals, computing the orthogonal components of conjugated quadratures of fields of the backscattered measurement beam; and using the two computed orthogonal components of conjugated quadratures of fields of the backscattered measurement beam to determine whether any defects or artifacts characterized by the characteristic dimension are present within the spot. Each of the first and second beams includes a first component and a second component that is orthogonal to the first component, wherein the selected parameter of the first beam is the phase of the second component of the first beam, and wherein the selected parameter of the second beam is the phase of the second component of the second beam. Alternatively, the selected parameter of the first beam is the frequency of the first beam, and the selected parameter of the second beam is the frequency of the second beam.

Still other embodiments include one or more of the following features. Using the interference signal for that selected location to determine whether any defects or artifacts are present involves jointly measuring two orthogonal components of conjugated quadratures of fields of the backscattered measurement beam. The method is implemented in an inspection tool wherein the object is a mask or a retilce. Alternatively, the method is implemented in a lithography tool wherein the object is a wafer or the object is a wafer stage and the artifacts are alignment marks.

In general, in another aspect, the invention features a method involving: focusing an incident measurement beam to a spot that illuminates a target area on or in the object to produce a backscattered measurement beam, the spot having a size L that is substantially larger than the characteristic dimension; interfering the backscattered measurement beam with a reference beam to produce an interference beam, said reference beam being oriented relative to the backscattered beam so as to produce a peak sensitivity for a portion of the backscattered beam that emanates from the object at a predetermined diffraction angle; converting the interference beam to an interference signal; and determining from the interference signal whether any defects or artifacts characterized by the characteristic dimension are present within the target area.

In general, in still another aspect, the invention features a method involving: generating a reference beam; generating a measurement beam for illuminating a spot on or in the object, the spot having a size L that is substantially larger than the characteristic dimension; and using the measurement and reference beams to interferometrically determine whether any defects or artifacts characterized by said characteristic dimension are present on or in the object.

An advantage of at least one embodiment of the invention is that one-, two-, and three-dimensional backscattered images of an object are generated with the measurement of conjugated quadratures of fields of backscattered beams by an object based on interferometric measurements.

Another advantage of at least one embodiment of the invention is that one-, two-, and three-dimensional backscattered images of an object are generated with joint measurements of conjugated quadratures of fields of backscattered beams by an object based on interferometric measurements.

Another advantage of at least one embodiment of the invention is that backscattered images of an object are generated with simultaneous measurements of conjugated quadratures of fields of backscattered beams by an array of a large number of spots in or on an object in interferometric measurements but with the components of the conjugated quadratures are not measured jointly.

Another advantage of at least one embodiment of the invention is that backscattered images of an object are generated with simultaneous measurements of joint measurements of conjugated quadratures of fields of backscattered beams by a large array of spots in or on an object in interferometric measurements.

Another advantage of at least one embodiment of the invention is that a bi- or quad-homodyne detection method can be used to obtain conjugated quadratures of fields of beams backscattered by a substrate that is being imaged.

Another advantage of at least one embodiment of the invention is that a variant of the bi- or quad-homodyne detection method can be used to obtain joint measurements of conjugated quadratures of fields of backscattered orthogonally polarized beams by a substrate that is being imaged.

Another advantage of at least one embodiment of the invention is that relative phase shifts between the arrays of reference and measurement beams can be introduced in certain embodiments of the invention by changing the frequencies of components of the input beam.

Another advantage of at least one embodiment of the invention is that relative phase shifts from a predetermined set of relative phase shifts can be introduced between the arrays of reference and measurement beams in certain embodiments of the invention.

Another advantage of at least one embodiment of the invention is backscattered imaging of a substrate with a sub-wavelength lateral resolution may be obtained with a working distance of the order of a mm.

Another advantage of at least one embodiment of the invention is backscattered imaging of a substrate with a sub-wavelength lateral resolution may be obtained with a working distance of the order of microns.

Another advantage of at least one embodiment of the invention is that the location of defects and artifacts may be obtained from the interferometric phase given by the corresponding the conjugated quadratures of high frequency spatial components of fields scattered by the defect and artifacts of an object.

Another advantage of at least one embodiment of the invention is backscattered imaging of an interior portion of a substrate with a sub-wavelength lateral resolution may be obtained with a working distance of the order of a mm.

Another advantage of at least one embodiment of the invention is backscattered imaging of an interior portion of a substrate with a sub-wavelength lateral resolution may be obtained with a working distance of the order of microns.

Another advantage of at least one embodiment of the invention is that the phases of the input beam components in certain embodiments of the invention do not affect measured conjugated quadratures of fields.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
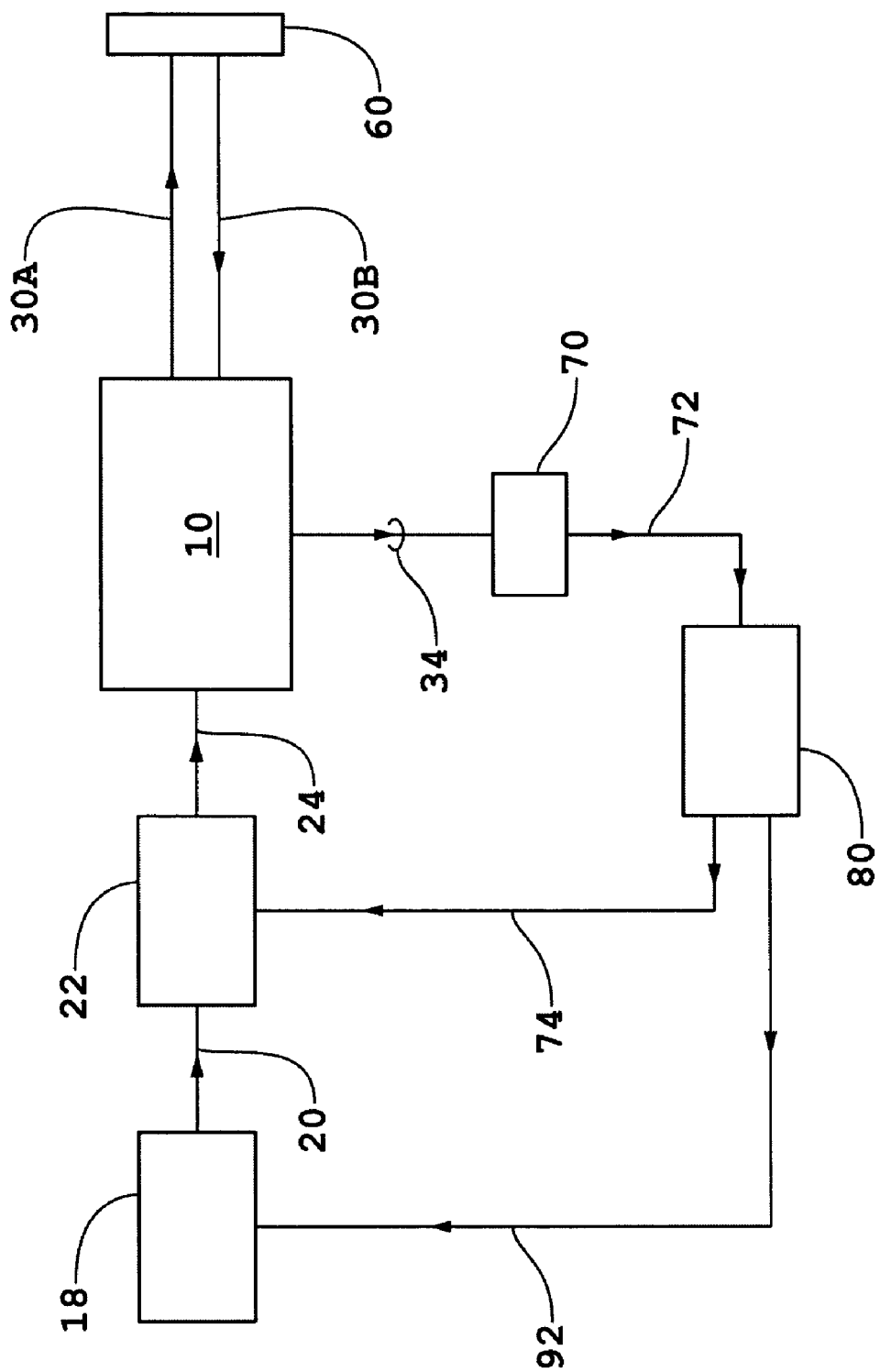
FIG. 1a is a diagram of an interferometric system.

An apparatus and method is described for measurement of a high frequency spatial component of conjugated quadratures of fields of a beam reflected/scattered by a spot of a two-dimensional section in or on a measurement object, e.g., an unpatterned or patterned wafer or lithography mask. The spot of the two-dimensional section may comprise a defect or artifact wherein a characteristic scale of the defect or artifact is less than the wavelength of the beam and is of the order of ½ to ¼ the spatial wavelength of the measured high frequency spatial component. The conjugated quadrature amplitudes of the high frequency spatial component are measured for the spot of the two-dimensional section where the characteristic dimension of the spot is approximately an order of magnitude or more larger than the spatial wavelength of the high frequency spatial component. The high frequency spatial component of reflected/scattered fields preferentially contains information about properties and locations of sub-wavelength defects and artifacts of the measurement object. Information about the locations is contained in the envelop function of the measured high frequency spatial component and in the interferometric phase given by the corresponding conjugated quadratures. The use of a spot with a characteristic dimension that is approximately an order of magnitude or more larger than the spatial wavelength of the high frequency spatial component in the measurement of the conjugated quadrature amplitudes permits a high speed scan of the section in a survey searching for sub-wavelength defects and/or to obtain information about properties of sub-wavelength defects and/or the artifacts. The apparatus and method for the measurement of high frequency spatial component comprises interferometric measurement of fields of backscattered beams by the object. The operation comprising measurement of conjugated quadratures of backscattered beams has the important property that the measurement of the high frequency spatial component is made operating in a dark field mode. The use of a dark field mode leads to an improved signal-to-noise ratio for measurement of the high frequency spatial component. In certain embodiments, information about backscattered fields is obtained for different polarization states of the measurement beams. Information about the backscattered fields is obtained from joint measurements of conjugated quadratures of the corresponding amplitudes using either a bi- or quad-homodyne detection method or variants thereof. The information about the backscattered fields is obtained from joint measurements of 2-dimensional arrays of conjugated quadratures in a scanning mode for a 100% coverage of a section.

A general description of the technique and procedure of the invention will first be given followed by a technical description of embodiments. The technique and procedure are based on the spatial frequency response of a two dimensional section of a substrate. The two-dimensional section may correspond to a surface of the substrate or to an internal two-dimensional section of the substrate. A substrate reflectance can be expanded into a Fourier series of spatial harmonics with each representing a spatial frequency component. The conjugated quadratures of the spatial frequency component represent properties of a two-dimensional section of the substrate. The conjugated quadratures of the spatial frequency component are written as $$F(x, y, \Lambda_x, \Lambda_y, \zeta_x, \zeta_y) = \qquad (1)$$
$$A(x, y, \Lambda_x, \Lambda_y, \zeta_x, \zeta_y) \times \cos\left(\frac{2\pi x}{\Lambda_x} + \zeta_x\right)\cos\left(\frac{2\pi y}{\Lambda_y} + \zeta_y\right),$$

$$\tilde{F}(x, y, \Lambda_x, \Lambda_y, \zeta_x, \zeta_y) = \qquad (2)$$
$$\tilde{A}(x, y, \Lambda_x, \Lambda_y, \zeta_x, \zeta_y) \times \sin\left(\frac{2\pi x}{\Lambda_x} + \zeta_x\right)\sin\left(\frac{2\pi y}{\Lambda_y} + \zeta_y\right)$$

where $F(x,y,\Lambda_x,\Lambda_y,\zeta_x,\zeta_y)$ and $\tilde{F}(x,y,\Lambda_x,\Lambda_y,\zeta_x,\zeta_y)$ are conjugated quadratures of the spatial frequency component, $A(x,y,\Lambda_x,\Lambda_y,\zeta_x,\zeta_y)$ and $\tilde{A}(x,y,\Lambda_x,\Lambda_y,\zeta_x,\zeta_y)$ are the amplitudes of the conjugated quadratures of the spatial frequency components, and $\Lambda_x$ and $\Lambda_y$ are the wavelengths of the spatial frequency components in the x and y directions, respectively, such that $1/\Lambda_x$ and $1/\Lambda_y$ are the corresponding spatial frequencies. Phase offsets $\zeta_x$ and $\zeta_y$ in Equations (1) and (2) are determined by the location of the source of the corresponding spatial frequency components in or on the two dimensional section of the substrate relative to a Cartesian coordinate system.

With respect to the embodiments described herein, the autocorrelation lengths of $A(x,y,\Lambda_x,\Lambda_y,\zeta_x,\zeta_y)$ and $\tilde{A}(x,y,\Lambda_x, \Lambda_y,\zeta_x,\zeta_y)$ in the x and y directions and/or of the respective envelop function are larger, e.g., a factor of three or an order of magnitude, than the smaller of the spatial wavelengths $\Lambda_x$ and $\Lambda_y$ and generally much less than corresponding dimensions of a two-dimensional section of a substrate being imaged. The autocorrelation lengths and the associated spatial wavelengths $\Lambda_x$ and $\Lambda_y$ are substantially independent parameters controlled by the design of the apparatus used in various embodiments of the invention.

Amplitudes of conjugated quadratures of a spatial frequency component of a substrate reflectance are measured interferometrically. The interferometric measurements will have a peak in detection sensitivity for defects and/or artifacts that have a characteristic dimension in the x direction of the order of $\Lambda_x/2$ to $\Lambda_x/4$ wherein it has been assumed that $\Lambda_x \leq \Lambda_y$ so as to illustrate important properties with a simplified description. Accordingly, the fractional spatial wavelength $\Lambda_x/4$ is preferably selected to be of the order of the corresponding characteristic dimension of defects and/or artifacts for which information is desired. For other spatial wavelengths, there will be a reduced sensitivity.

It is of particular interests to note that in addition to a peak in detection sensitivity for defects and/or artifacts that have a corresponding characteristic dimension of the order of $\Lambda_x/4$, the detection sensitivity will be substantially zero for a corresponding zero spatial frequency component. The zero sensitivity for detection of the corresponding zero spatial frequency component permits a particularly important mode of operation, a dark field interferometric mode. In the dark field interferometric mode, the measurements of the amplitudes $A(x,y,\Lambda_x,\Lambda_y,\zeta_x,\zeta_y)$ and $\tilde{A}(x,y,\Lambda_x,\Lambda_y,\zeta_x,\zeta_y)$ are made with a significantly increased signal-to-noise ratio (see for example the discussion of statistical noise in commonly owned U.S. Pat. No. 5,760,901 (ZI-05) entitled "Method And Apparatus For Confocal Interference Microscopy With Background Amplitude Reduction And Compensation" and U.S. Pat. No. 6,480,285 B1 (ZI-08) entitled "Multiple Layer Confocal Interference Microscopy Using Wavenumber Domain Reflectometry And Background Amplitude Reduction And Compensation" wherein both are by Henry A. Hill, the contents of which are incorporated herein in their entirety by reference.

It is also of particular interest to note that the interferometric phase corresponding to amplitude and phase representation of the measured conjugated quadratures of the high frequency spatial components is sensitive in general to displacements of imaged defects and artifacts in the x and y directions as well as in the z direction. This property makes it possible to determine locations of defects and artifacts through measurements of a phase which consequently possess the advantages generally assigned to measuring displacements with linear displacement interferometer.

The amplitude of the measured conjugated quadratures of the high frequency spatial frequency components is sensitive to the scattering cross section of the respective defects and artifacts. The scattering cross section is sensitive to the size and composition of the defects and artifacts.

Figure 3:
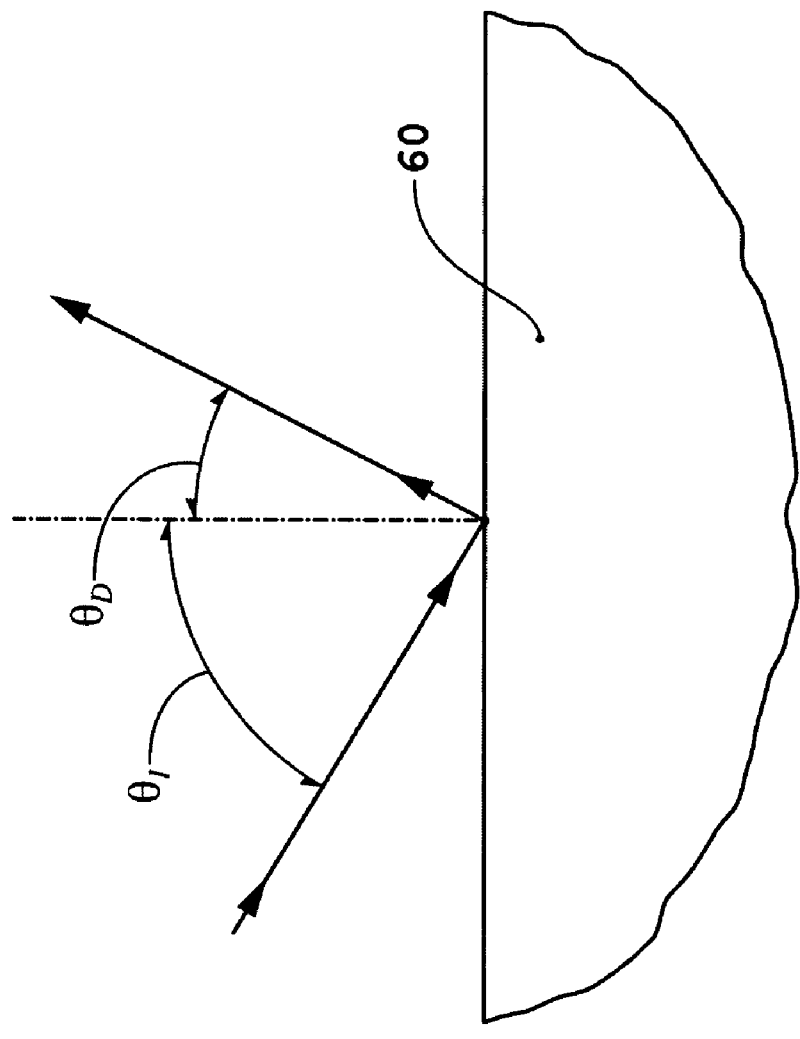
FIG. 3 is a diagram of the angles of incidence and diffraction of beams.

Because of the characteristic size of the spot being imaged is larger than the wavelength of the spatial frequency components, the spatial frequency components will be preferentially diffracted at particular angles in respective planes. For a given optical wavelength $\lambda$ for a measurement beam, the particular angle at which a spatial frequency component of the substrate reflectance will diffract the beam in a corresponding plane is given by a grating equation $$\Lambda[\sin\theta_I - \sin\theta_D] = \lambda \quad (3)$$

where $\theta_I$ and $\theta_D$ are angles of incidence and diffraction as shown diagrammatically in FIG. 3. It is evident from Equation (3) that in order to obtain the smallest $\Lambda$ for a given optical wavelength $\lambda$, $$\theta_D \cong -\theta_I, \quad (4)$$

$$\theta_I \cong 1. \quad (5)$$

The width $\Delta\theta$ of the beam diffracted by the spatial frequency component of the substrate reflectance will be determined by an autocorrelation length l of $A(x,y,\Lambda_x,\Lambda_y,\zeta_x,\zeta_y)$ and $\tilde{A}(x,y,\Lambda_x,\Lambda_y,\zeta_x,\zeta_y)$ as $$\Delta\theta \cong \frac{\lambda}{l}\sec\theta_R. \quad (6)$$

The autocorrelation length l is determined by properties of an imaging system that determines the dimensions of the spot being imaged.

The defects in or on a patterned wafer are identified by comparing the measured array of conjugated quadratures $A(x,y,\Lambda_x,\Lambda_y,\zeta_x,\zeta_y)$ and $\tilde{A}(x,y,\Lambda_x,\Lambda_y,\zeta_x,\zeta_y)$ with a master array of conjugated quadratures generated by a master patterned wafer that does not have any defects.

In order to reduce the density of measurements of $A(x,y,\Lambda_x,\Lambda_y,\zeta_x,\zeta_y)$ and $\tilde{A}(x,y,\Lambda_x,\Lambda_y,\zeta_x,\zeta_y)$ required for a full coverage of a substrate section, the autocorrelation length l is selected to be larger than $\Lambda_x$ by a factor $\zeta$ that is the order of 10 or more. Thus, a full survey of the substrate section can be obtained for the presence of defects and/or artifacts of characteristic dimensions of $\Lambda_x/4$ or smaller with a time reduced by a factor of $\zeta^2$ compared to the time required to execute a full survey of the substrate surface with an image resolution of $\approx\lambda/4$.

The sampling frequency for the measurement of $A(x,y,\Lambda_x,\Lambda_y,\zeta_x,\zeta_y)$ and $A(x,y,\Lambda_x,\Lambda_y,\zeta_x,\zeta_y)$ is preferably approximately equal to twice the spatial frequency $1/l$, i.e., $2/l$. In addition, the sampling spatial frequency is preferably selected to correspond to the spatial frequency of the pitch of pixel location of a CCD detector in the x direction.

The survey can locate the positions of defects and/or artifacts for example by two different data analysis techniques. The amplitudes $A(x,y,\Lambda_x,\Lambda_y,\zeta_x,\zeta_y)$ and $\tilde{A}(x,y,\Lambda_x,\Lambda_y,\zeta_x,\zeta_y)$ in Equations (1) and (2) are indicated as being dependent on the x and y coordinates and as also containing information about the location of the source of the spatial frequency components. The spatial resolution of one of the analysis techniques corresponds to approximately the autocorrelation length l. In this case, the information about the location of the source is contained in the envelop function represented by the magnitude $$\{[A(x,y,\Lambda_x,\Lambda_y,\zeta_x,\zeta_y)]^2 + [\tilde{A}(x,y,\Lambda_x,\Lambda_y,\zeta_x,\zeta_y)]^2\}^{1/2}$$

of the spatial frequency components.

If a higher spatial resolution is required in an end use application after the defects and/or artifacts are located with a spatial resolution of approximately l, the locations can be determined made by the second analysis technique mod $\Lambda_x$ and $\Lambda_y$ in the x and y directions, respectively, with a spatial resolution of approximately $\lambda/2$ to $\lambda/4$ when using properties of the sinusoidal varying components of the conjugated quadratures or the interferometric phase of the measured conjugated quadratures in a amplitude and phase representation thereof. Alternatively, the location information acquired in the survey can be used as input information of a subsequent measurement with an interferometric confocal microscope such as described in commonly owned U.S. patent application Ser. No. 10/778,371 (ZI-40) entitled "Transverse Differential Interferometric Confocal Microscopy;" U.S. Provisional Application No. 60/459,425 (ZI-50) entitled "Apparatus and Method for Joint Measurement of Fields of Scattered/Reflected Orthogonally Polarized Beams by an Object in Interferometry;" U.S. patent application Ser. No. 10/816,180 (ZI-50) filed Apr. 1, 2004 and entitled "Apparatus and Method for Joint Measurement Of Fields Of Scattered/Reflected Or Transmitted Orthogonally Polarized Beams By An Object In Interferometry;" U.S. Provisional Application No. 60/460,129 (ZI-51) entitled "Apparatus and Method for Measurement of Fields of Forward Scattered/Reflected and Backscattered Beams by an Object in Interferometry," and U.S. patent application Ser. No. 10/816,172, (ZI-51) filed Apr. 1, 2004 and entitled "Apparatus And Method For Measurement Of Fields Of Forward Scattered/ Reflected and Backscattered Beams By An Object In Interferometry" of which each are to Henry A. Hill and of which the contents of the two cited provisional patent applications and of the three patent applications are herein incorporated in their entirety by reference.

The substrate reflectance will in general be sensitivity to the polarization of the measurement beam incident on the substrate. Accordingly, the amplitudes of conjugated quadratures $A(x,y,\Lambda_x,\Lambda_y,\zeta_x,\zeta_y)$ and $\tilde{A}(x,y,\Lambda_x,\Lambda_y,\zeta_x,\zeta_y)$ will be a function of the polarization of the measurement beam incident on the substrate. The polarization sensitive properties of the amplitudes of conjugated quadratures $A(x,y,\Lambda_x,\Lambda_y,\zeta_x,\zeta_y)$ and $\tilde{A}(x,y,\Lambda_x,\Lambda_y,\zeta_x,\zeta_y)$ may be measured in various embodiments of the invention.

Some of the embodiments described herein may be used to measure propagation of signals, e.g., thermal or acoustical, in a section by using a probe beam in addition to the measurement beam where the probe beam precedes the measurement beam by a time $\tau$. The probe beam and the measurement beams may have different optical wavelengths. An advantage of using those embodiments to measure temporal response of the substrate is the high spatial frequency resolution in the plane of the section.

In the following description of different embodiments, many elements of the different embodiments perform like functions and are indicated with the same numerals in different respective figures of the embodiments.

A general description of embodiments incorporating the present invention will first be given for interferometer systems wherein the bi- and quad-homodyne detection methods and variants thereof are used in interferometer systems for making joint measurements of conjugated quadratures of fields of beams backscattered by a measurement object. Referring to FIG. 1a, an interferometer system is shown diagrammatically comprising an interferometer 10, a source 18, a beam-conditioner 22, detector 70, an electronic processor and controller 80, and a measurement object or substrate 60. Source 18 is a pulsed or shuttered source that generates input beam 20 comprising one or more frequency components. Beam 20 is incident on and exits beam-conditioner 22 as input beam 24 that comprises a single polarized component or two orthogonally polarized components. Each of the orthogonally polarized components comprises two or more different frequency components. The measurement beam components of the frequency components of input beam 24 are coextensive in space and have the same temporal window function and the corresponding reference beam components are coextensive in space and have the same temporal window function although the measurement beam components and the reference beam components may not be spatially coextensive.

Reference and measurement beams may be generated in either beam-conditioner 22 from a set of beams or in interferometer 10 for each of the two or more frequency components of input beam 24. Measurement beam 30A generated in either beam-conditioner 22 or in interferometer 10 is incident on substrate 60. Measurement beam 30B is a return measurement beam generated as either a portion of measurement beam 30A reflected and/or scattered by substrate 60. Return measurement beam 30B is combined with the reference beam in interferometer 10 to form output beam 34.

Output beam 34 is detected by detector 70 to generate either one or more electrical interference signals per source pulse for the bi-homodyne or quad-homodyne detection methods or variants thereof as signal 72. Detector 70 may comprise an analyzer to select common polarization states of the reference and return measurement beam components of beam 34 to form a mixed beam. Alternatively, interferometer 10 may comprise an analyzer to select common polarization states of the reference and return measurement beam components such that beam 34 is a mixed beam.

In the practice, known phase shifts are introduced between the reference and measurement beam components of output beam 34 by two different techniques. In the first technique, phase shifts are introduced between corresponding reference and measurement beam components for each of the frequency components of output beam 34 as a consequence of a non-zero optical path difference between the reference and measurement beam paths in interferometer 10 and corresponding frequency shifts introduced to the frequency components of input beam 24 by beam-conditioner 22 and/or source 18 as controlled by signals 74 and 92 from electronic processor and controller 80. In the second technique, phase shifts are introduced between the reference and measurement beam components for each of the frequency components of input beam 24 by beam-conditioner 22 as controlled by signals 74 and 92 from electronic processor and controller 80.

There are different ways to configure source 18 and beam-conditioner 22 to meet the input beam requirements of the different embodiments of the present invention. Examples of beam-conditioners that may be used in either first or the second technique comprise combinations of a two frequency generator and phase shifting type of beam-conditioner such as described in commonly owned U.S. Provisional Patent Application No. 60/442,858 (ZI-47) entitled "Apparatus and Method for Joint Measurements of Conjugated Quadratures of Fields of Reflected/Scattered Beams by an Object in Interferometry" and U.S. patent application Ser. No. 10/765,368, filed Jan. 27, 2004 (ZI-47) and entitled "Apparatus and Method for Joint Measurements of Conjugated Quadratures of Fields of Reflected/Scattered and Transmitted Beams by an Object in Interferometry" of which both are to Henry A. Hill and of which the contents of provisional and non-provisional applications are herein incorporated in their entirety by reference.

Another example of beam-conditioner that may be used in either the first or the second technique comprise combinations of multiple frequency generators and phase shifting types of beam-conditioners such as subsequently described herein with respect to FIG. 1e.

With a continuation of the description of different ways to configure source 18 and beam-conditioner 22 to meet the input beam requirements of different embodiments of the present invention, source 18 will preferably comprise a pulsed source. There are a number of different ways for producing a pulsed source [see Chapter 11 entitled "Lasers", *Handbook of Optics*, 1, 1995 (McGraw-Hill, New York) by W. Silfvast]. Each pulse of source 18 may comprise a single pulse or a train of pulses such as generated by a mode locked Q-switched Nd:YAG laser. A single pulse train is referenced herein as a pulse and a pulse and a pulse train are used herein interchangeably.

Source 18 may be configured in certain embodiments of the present invention to generate two or more frequencies by techniques such as described in a review article entitled "Tunable, Coherent Sources For High-Resolution VUV and XUV Spectroscopy" by B. P. Stoicheff, J. R. Banic, P. Herman, W. Jamroz, P. E. LaRocque, and R. H. Lipson in *Laser Techniques for Extreme Ultraviolet Spectroscopy*, T. J. McIlrath and R. R. Freeman, Eds., (American Institute of Physics) p 19 (1982) and references therein. The techniques include for example second and third harmonic generation and parametric generation such as described in the articles entitled "Generation of Ultraviolet and Vacuum Ultraviolet Radiation" by S. E. Harris, J. F. Young, A. H. Kung, D. M. Bloom, and G. C. Bjorklund in *Laser Spectroscopy I*, R. G. Brewer and A. Mooradi, Eds. (Plenum Press, New York) p 59, (1974) and "Generation of Tunable Picosecond VUV Radiation" by A. H. Kung, *Appl. Phys. Lett.* 25, p 653 (1974). The contents of the three cited articles are herein incorporated in their entirety by reference.

The output beams from source 18 comprising two or more frequency components may be combined in beam-conditioner 22 by beam-splitters to form coextensive measurement and reference beams that are either spatially separated or coextensive as required in certain embodiments of the present invention. The frequency shifting of the various components required in certain embodiments of the present invention may be introduced in source 18 for example by frequency modulation of input beams to parametric generators and the phase shifting of reference beams relative to measurement beams in beam-conditioner 22 may be achieved by phase shifters of the optical-mechanical type comprising for example prisms or mirrors and piezoelectric translators or of the electro-optical modulator type.

The general description is continued with reference to FIG. 1*a*. Input beam 24 is incident on interferometer 10 wherein reference beams and measurement beams are generated. The reference beams and measurement beams comprise one or two arrays of reference beams and one or two arrays of measurement beams, respectively, for measurements using measurement beams that comprise a single polarization state or two orthogonal polarization states, respectively, wherein the arrays may comprise arrays of one element. The arrays of measurement beams are focused on and/or in measurement object 60 and arrays of return measurement beams are generated by reflection/scattering by measurement object 60. The arrays of reference beams and return measurement beams are combined by a beam-splitter to form one or two arrays of output beams using measurement beams that comprise a single polarization state or two orthogonal polarization states, respectively. The arrays of output beams are mixed with respect to state of polarization either in interferometer 10 or in detector 70. The arrays of output beams are subsequently focused to spots on pixels of a multipixel detector and detected to generate the array of electrical interference signals 72.

The conjugated quadratures of fields of return measurement beams are obtained by using a single-, double-, bi-, quad-homodyne detection method or variants thereof. The bi- and quad-homodyne detection methods are described for example in cited U.S. Provisional Patent Application No. 60/442,858 (ZI-47) and U.S. patent application Ser. No. 10/765,368, filed Jan. 27, 2004 (ZI-47) and entitled "Apparatus and Method for Joint Measurements of Conjugated Quadratures of Fields of Reflected/Scattered and Transmitted Beams by an Object in Interferometry". The variants of the bi- and quad-homodyne detection methods are described for example in cited U.S. Provisional Patent Application No. 60/459,425 (ZI-50) and U.S. patent application Ser. No. 10/816,180, filed Apr. 1, 2004 (ZI-50) and entitled "Apparatus and Method for Joint Measurement of Fields of Scattered/Reflected Orthogonally Polarized Beams by an Object in Interferometry".

For the single-homodyne detection method, input beam 24 comprises a single frequency component and sets of four or eight measurements of the array of electrical interference signals 72 is made in non-ellipsometric or ellipsometric measurements, respectively, wherein non-ellipsometric and ellipsometric measurements correspond to measurements made with a measurement beam 30A comprising a single polarized component or orthogonally polarized components, respectively. For each of the measurements of the array of electrical interference signals 72 in non-ellipsometric and ellipsometric measurements, known phase shifts are introduced between each reference beam component and respective return measurement beam component of output beam 34. The subsequent data processing procedure used to extract the conjugated quadratures of fields of beams reflected and/or scattered by a substrate is subsequently described herein with respect to the first embodiment of the present invention and also for example in commonly owned U.S. Pat. No. 6,445,453 (ZI-14) entitled "Scanning Interferometric Near-Field Confocal Microscopy" by Henry A. Hill of which the contents are incorporated herein in their entirety by reference.

The double-homodyne detection method which is applicable to non-ellipsometric measurements uses input beam 24 comprising four frequency components and four detectors to obtain measurements of electrical interference signals that are subsequently used to obtain conjugated quadratures in non-ellipsometric measurements. Each detector element of the four detector elements obtains a different one of the four electrical interference signal values with the four electrical interference signal values obtained simultaneously to compute the conjugated quadratures for a field. Each of the four electrical interference signal values contains only information relevant to one orthogonal component of the conjugated quadratures. The double-homodyne detection used herein is related to the detection methods such as described in Section IV of the article by G. M D'ariano and M G. A. Paris entitled "Lower Bounds On Phase Sensitivity In Ideal And Feasible Measurements," *Phys. Rev. A* 49, 3022–3036 (1994). Accordingly, the double-homodyne detection method does not make joint determinations of conjugated quadratures of fields wherein each electrical interference signal value contains information simultaneously about each of two orthogonal components of the conjugated quadratures.

In the adaptation of the double-homodyne detection method to ellipsometric measurements, input beam 24 comprises eight frequency components and eight detectors to obtain measurements of eight electrical interference signals that are subsequently used to obtain conjugated quadratures. Each detector element of the eight detector elements obtains a different one of the eight electrical interference signal values with the eight electrical interference signal values obtained simultaneously to compute the conjugated quadratures of fields of scattered/reflected orthogonally polarized fields. Each of the eight electrical interference signal values contains only information relevant to one orthogonal component of one of the two conjugated quadratures.

The bi- and quad-homodyne detection methods obtain measurements of electrical interference signals wherein each measured value of an electrical interference signal contains simultaneously information about two orthogonal components of conjugated quadratures. The two orthogonal components correspond to orthogonal components of conjugated quadratures such as described in cited U.S. Provisional Patent Application No. 60/442,858 (ZI-47) and cited U.S. patent application Ser. No. 10/765,368, filed Jan. 27, 2004 (ZI-47) entitled "Apparatus and Method for Joint Measurements of Conjugated Quadratures of Fields of Reflected/Scattered and Transmitted Beams by an Object in Interferometry".

The variants of the bi- and quad-homodyne detection methods obtain measurements of electrical interference signals wherein each measured value of an electrical interference signal contains simultaneously information about two orthogonal components of each of two conjugated quadratures of fields of scattered/reflected orthogonally polarized beams. The two orthogonal components of the two conjugated quadratures correspond to orthogonal components of conjugated quadratures such as described in cited U.S. Provisional Patent Application No. 60/459,425 (ZI-50) and cited U.S. patent application Ser. No. 10/816,180, filed Apr. 1, 2004 (ZI-50) and entitled "Apparatus and Method for Joint Measurement of Fields of Scattered/Reflected Orthogonally Polarized Beams by an Object in Interferometry".

Figure 1B:
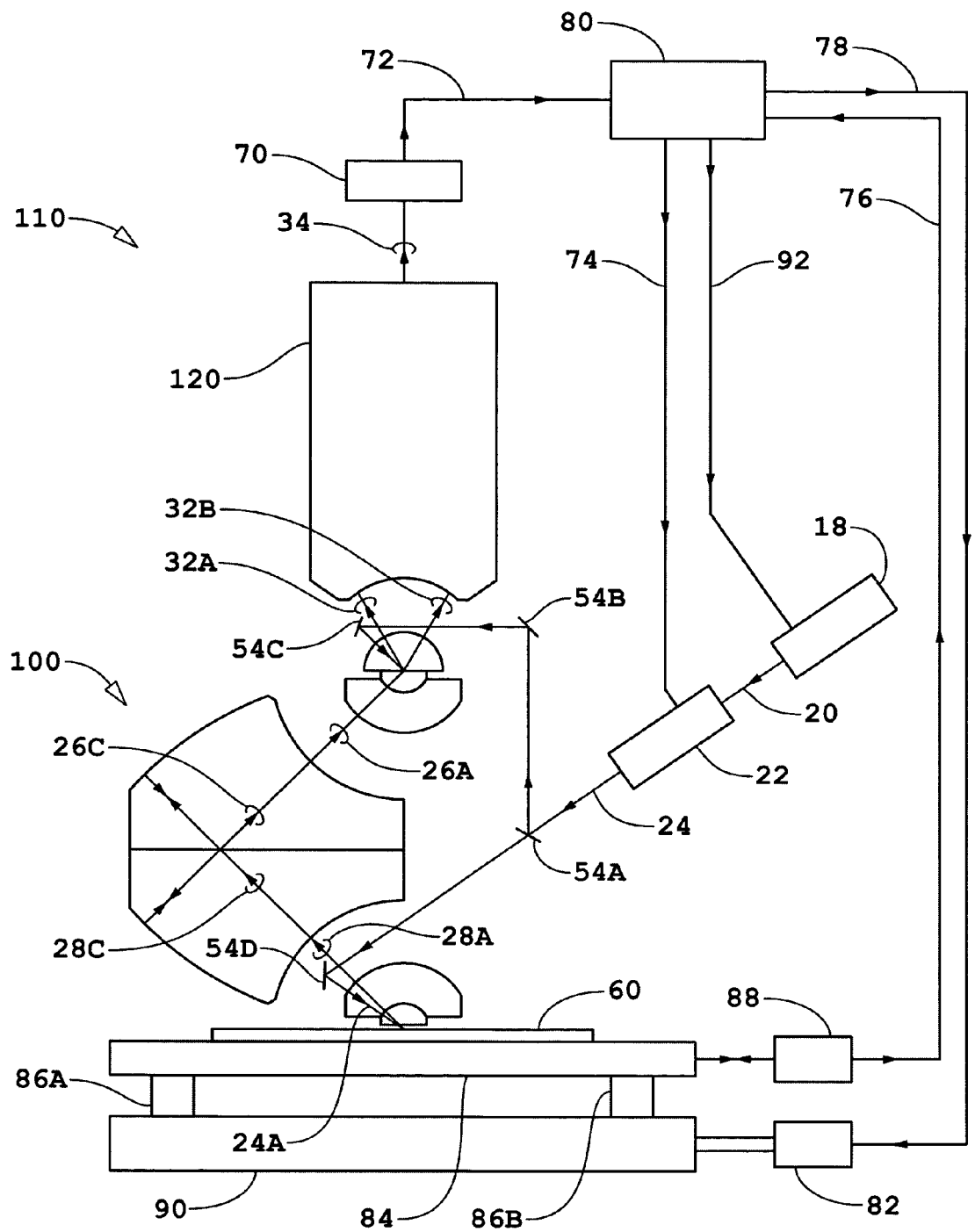
FIG. 1b is a schematic diagram of an embodiment of mask or reticle inspection tool and an embodiment of a wafer/stage inspection portion of a lithography tool with the exposure optic and source omitted that comprises an interferometric metrology system which in turn comprises a catadioptric imaging system.

A first embodiment of the present invention is shown schematically in FIG. 1b. The schematic diagram in FIG. 1b is of mask or reticle inspection tool or an diagram of a wafer/stage inspection portion of a lithography tool (with the exposure optic and source omitted) used to measure locations of artifacts on wafers and/or a stage such as alignment marks. The first embodiment comprises a first imaging system generally indicated as numeral 100, pinhole array beam-splitter 12, detector 70, and a second imaging system generally indicated as numeral 110. The second imaging system 110 is low power microscope having a large working distance, e.g. Nikon ELWD and SLWD objectives and Olympus LWD, ULWD, and ELWD objectives.

Figure 1C:
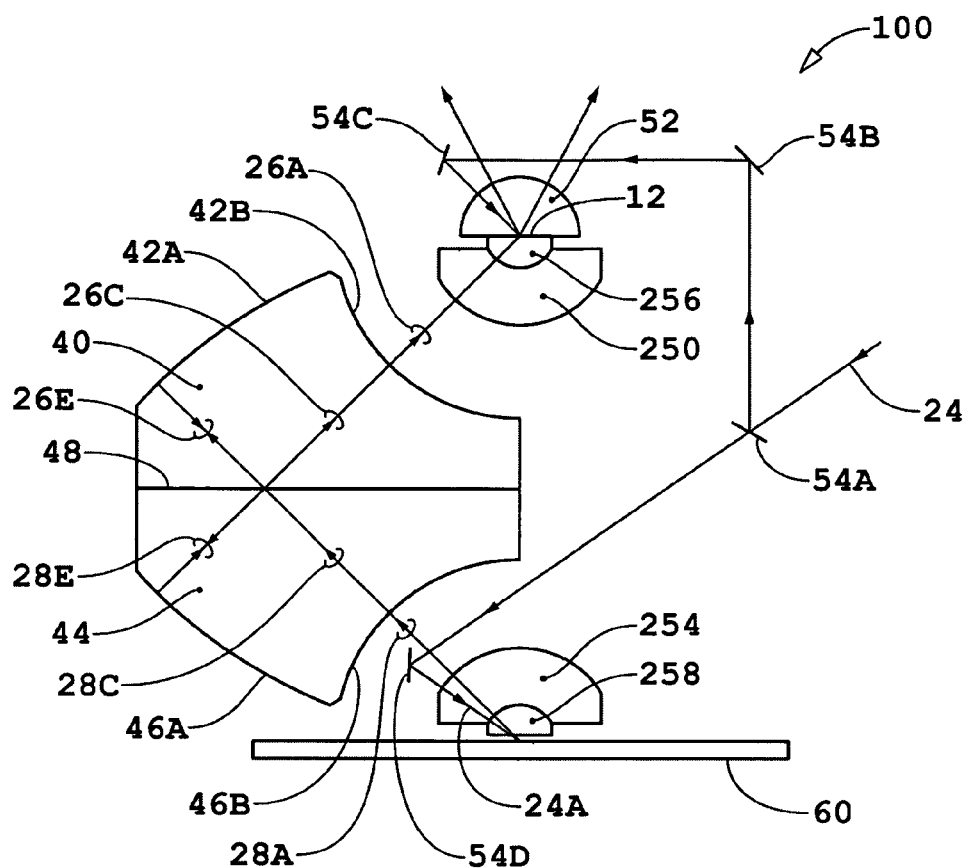
FIG. 1c is a diagram of a catadioptric imaging system.

The first imaging system 100 is shown schematically in FIG. 1c. The imaging system 100 is a catadioptric system such as described in commonly owned U.S. Pat. No. 6,552,852 B2 (ZI-38) and U.S. Pat. No. 6,717,736 (ZI-43) of which both are entitled "Catoptric and Catadioptric Imaging System," both applications are to Henry A. Hill, and the contents of the two cited patents are incorporated herein in their entirety by reference.

Figure 2A:
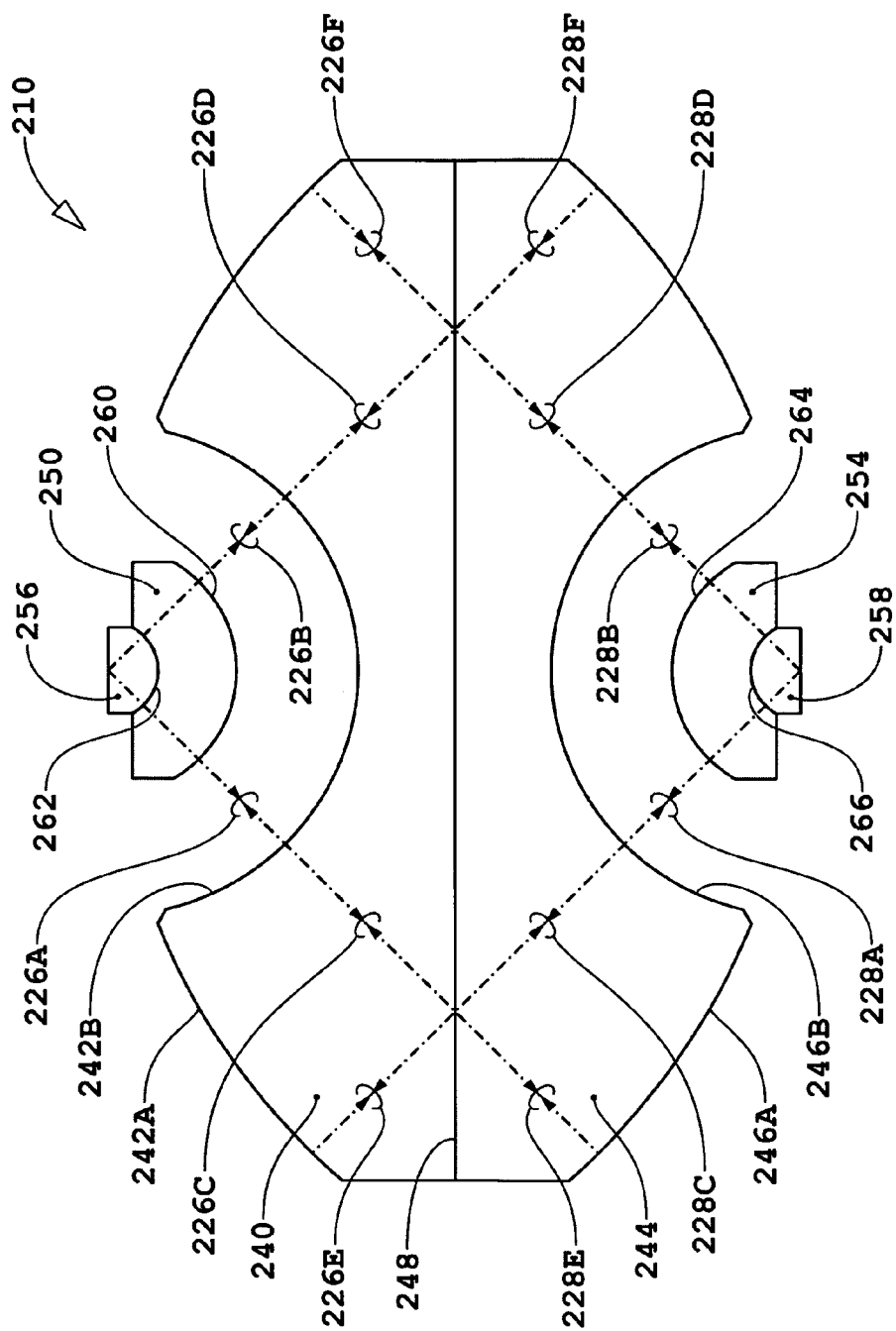
FIG. 2a is a schematic diagram of an achromatic astigmatic catadioptric imaging system.

Catadioptric imaging system 100 comprises a section, e.g., a pie section, of catadioptric imaging system 210 shown schematically in FIG. 2a. Elements of catadioptric imaging system 210 shown in FIG. 2a comprise two different media in order to generate an achromatic anastigmat. Catadioptric imaging system 210 comprises catadioptric elements 240 and 244, beam-splitter 248, concentric lenses 250 and 254, and plano convex lenses 256 and 258. Surfaces 242A and 246A are convex spherical surfaces with nominally the same radii of curvature and the respective centers of curvature of surfaces 242A and 246A are conjugate points with respect to beam-splitter 248. Surfaces 242B and 246B are concave spherical surfaces with nominally the same radii of curvature. The centers of curvature of surfaces 242B and 246B are the same as the centers of curvature of surfaces 246A and 242A, respectively.

The centers of curvature of the surfaces of concentric lens 250 and plano convex lens 256 are nominally the same as the center of curvature of surfaces 242B and 246A. The centers of curvature of the surfaces of concentric lens 254 and plano convex lens 258 are nominally the same as the center of curvature of surfaces 242A and 246B. The radii of curvature of surfaces 260 and 264 are nominally the same and the radii of curvature of surfaces 262 and 266 are nominally the same. There may be a small gap between the convex surface and corresponding concave surface of lenses 256 and 250, respectively, and there may be a corresponding small gap between the convex surface and corresponding concave surface of lenses 258 and 254, respectively.

Figure 2B:
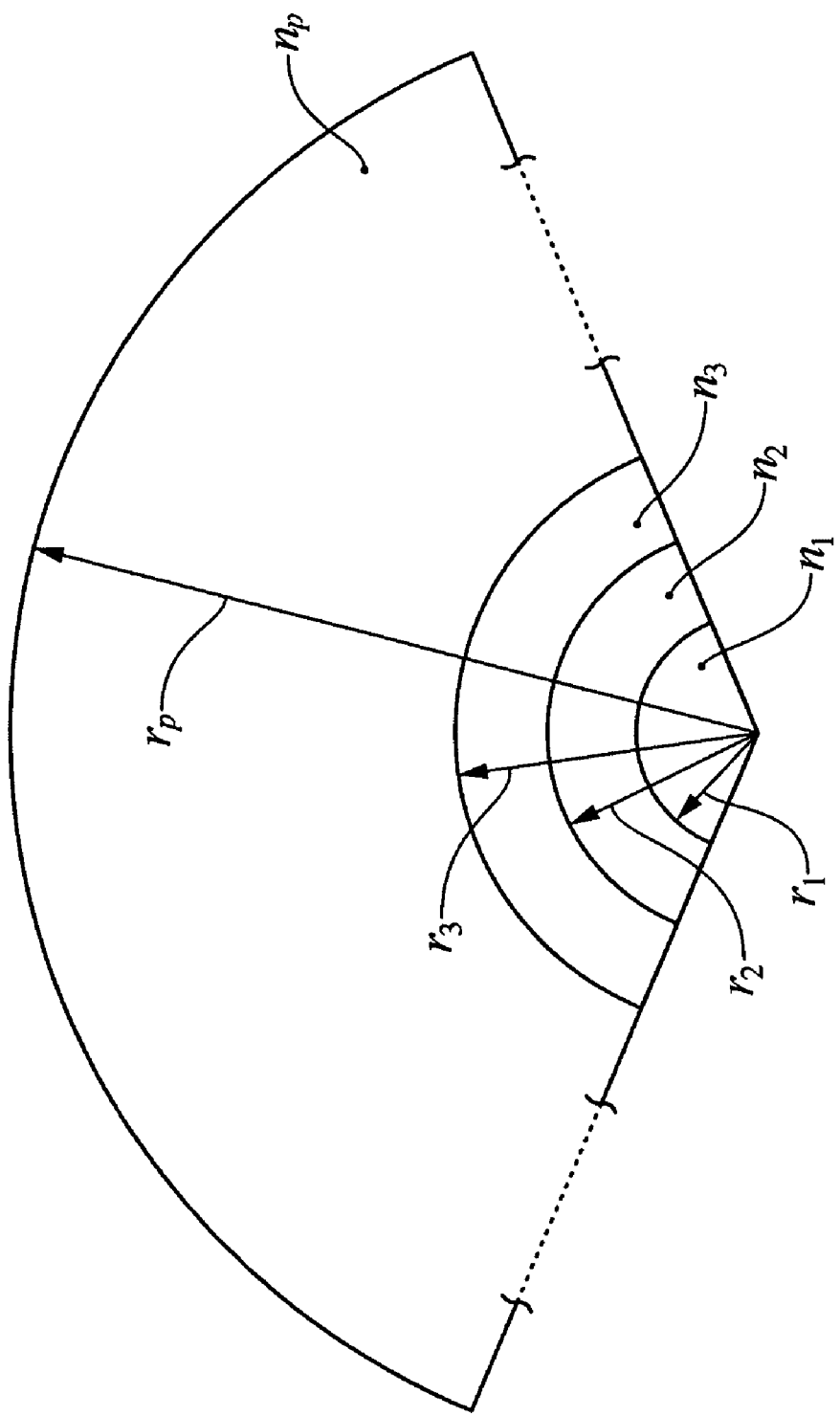
FIG. 2b is a diagram showing surfaces and corresponding radii of a catadioptric imaging system.

The sagittal field of catadioptric imaging system 210 is a flat field and the tangential field is also a flat field for a certain object field when the Petzval sum is zero, i.e., $$2\sum_{j=1}^{p-1}\left(\frac{1}{n_j}-\frac{1}{n_{j+1}}\right)\frac{1}{r_j}+\frac{1}{n_p}\frac{2}{r_p}=0 \qquad (7)$$

where $r_j$ is the radius of curvature of surface j, $r_p$ is the radius of curvature of the mirror surface, and $n_j$ is the index of refraction of the media located on the beam incidence side of surface j such as shown diagrammatically in FIG. 2b. The condition for the generation of an achromatic anastigmat at wavelength $\lambda_c$ is accordingly given by the equation $$\frac{\partial\left[2\sum_{j=1}^{p-1}\left(\frac{1}{n_j}-\frac{1}{n_{j+1}}\right)\frac{1}{r_j}+\frac{1}{n_p}\frac{2}{r_p}\right]}{\partial\lambda}=0. \qquad (8)$$

Two considerations in the selection of the radii of curvature of surfaces 242B and 246B and surfaces 262 and 266 are the area of the system pupil function of the imaging system 210 and the size of the object field that can be effectively used with respect to image quality. The first two considerations place competing demands of the selection of the radii of curvature of surfaces 242B and 246B and surfaces 262 and 266. Third and fourth considerations are with respect to the conditions set out in Equations (7) and (8). A fifth consideration in the selection of the media of the lenses of imaging system 210 is the transmission properties of the media for the range of wavelengths to be used in an end use application.

For an example of an achromatic anastigmat design for deep UV operation, the media of elements 240, 244, 256, and 258 is selected as $CaF_2$ and the media of concentric lenses 252 and 254 is selected as a UV grade fused silica or fluorine-doped fused silica (F—$SiO_2$). Other parameters of the example achromatic anastigmat design such as the radii of curvature of surfaces are listed in Table 1 for $\lambda_c=250$ nm. With this choice of media, the operation range is down to 170 nm for UV grad fused silica and down to 155 nm for F—$SiO_2$. For the achromatic anastigmat design parameters listed in Table 1, the contribution of geometric ray tracing effects is ≦40 nm for an object field of 1.5 mm in diameter and a numerical aperture NA=0.970 in the object space just outside of the plane surface of plano convex lens 258.

TABLE 1

Achromatic Anastigmat Design for $\lambda_c$ = 250 nm

| Media | j | $n_j$ | $r_j$ (mm) |
|---|---|---|---|
| $CaF_2$ | 1 | 1.467297 | 3.600 |
| Fused Silica | 2 | 1.507446 | 9.256 |
| Vacuum | 3 | 1 | 18.000 |
| $CaF_2$ | 4 | 1.467297 | 50.000 |

Figure 2C:
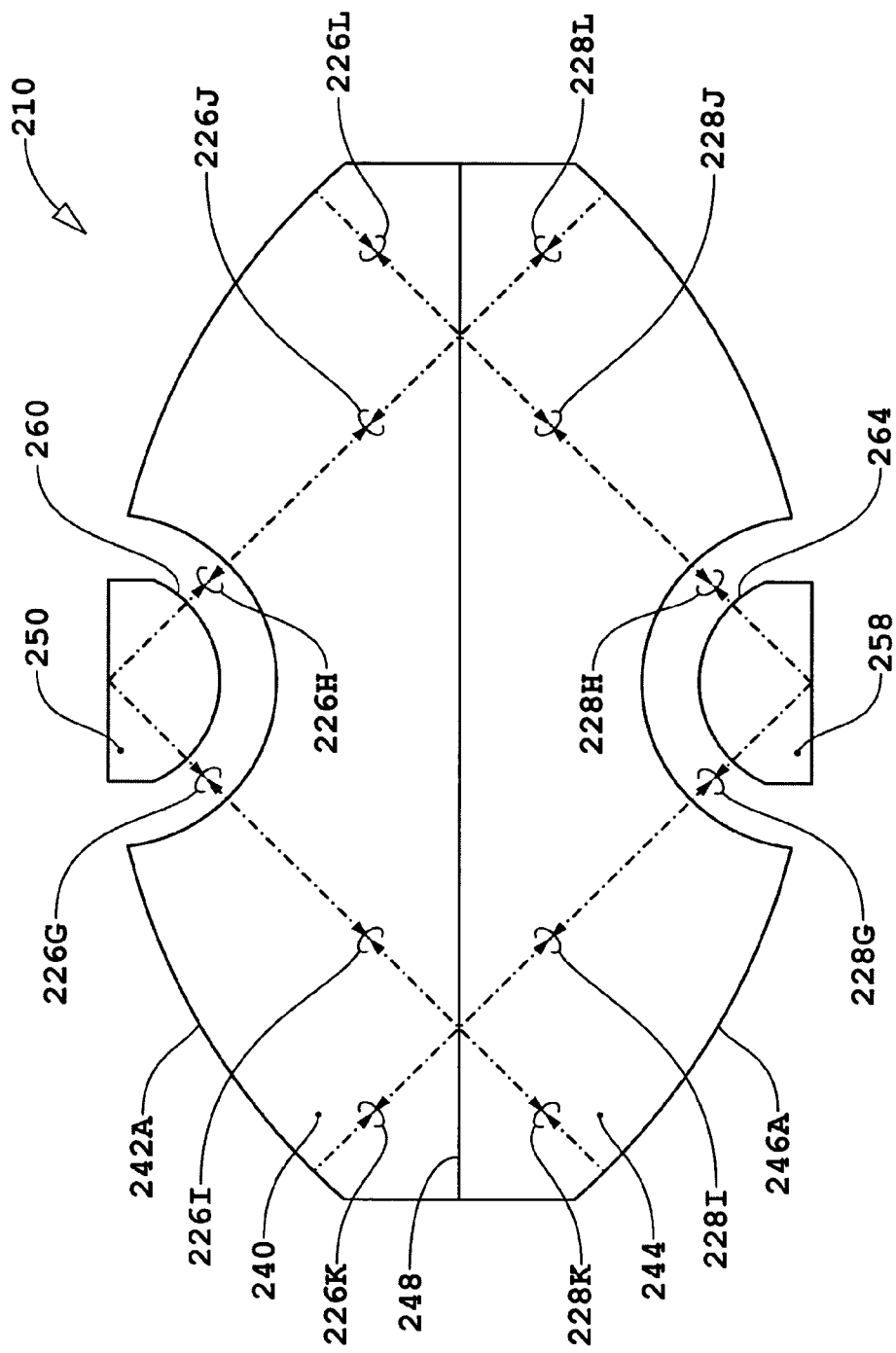
FIG. 2c is a schematic diagram an astigmatic catadioptric imaging system.

A variant of catadioptric imaging system 210 is shown in FIG. 2c wherein catadioptric imaging system 100 is an anastigmat that is not achromatic. The media of elements 140 and 144 may comprise $CaF_2$, $BaF_2$, or $SrF_2$ for work down to 140 nm and UV grade fused silica for operation to 180 nm. The respective radii of curvature for anastigmat design at λ=250 nm using $CaF_2$ are listed in Table 2. For the anastigmat design listed in Table 2, the contribution of geometric ray tracing effects is $\leq 40$ nm for an object field of 1.5 mm and a numerical aperture NA=0.970 in the object space just outside of the plane surface of plano convex lens 258.

TABLE 2

Anastigmat Design for λ = 250 nm

| Media | j | $n_j$ | $r_j$ (mm) |
|---|---|---|---|
| $CaF_2$ | 1 | 1.467297 | 7.950 |
| Air | 2 | 1 | 12.000 |
| $CaF_2$ | 3 | 1.467297 | 50.000 |

The respective radii of curvature for anastigmat design at λ=250 nm using fused silica are listed in Table 3. For the anastigmat design listed in Table 3, the contribution of geometric ray tracing effects is $\leq 40$ nm for an object field of 1.5 mm and a numerical aperture NA=0.970 in the object space just outside of the plane surface of plano convex lens 258.

TABLE 3

Anastigmat Design for λ = 250 nm

| Media | j | $n_j$ | $r_j$ (mm) |
|---|---|---|---|
| Fused Silica | 1 | 1.467297 | 7.950 |
| Air | 2 | 1 | 12.000 |
| Fused Silica | 3 | 1.467297 | 50.000 |

Intrinsic birefringence of $SrF_2$ is less than the intrinsic birefringence of $CaF_2$ and $BaF_2$ at 140 nm. However, the intrinsic birefringence of any one of the three crystalline materials can be accommodated in the catadioptric imaging system 100 since only an azimuthal section of the lens elements are used and that section can be selected to significantly reduce the effects of intrinsic birefringence, e.g., with the [111] axis of the crystal aligned parallel to the optic axis of catadioptric imaging system 100 and the [110] axis of the crystal aligned parallel to the plane of FIG. 2a.

Figure 2D:
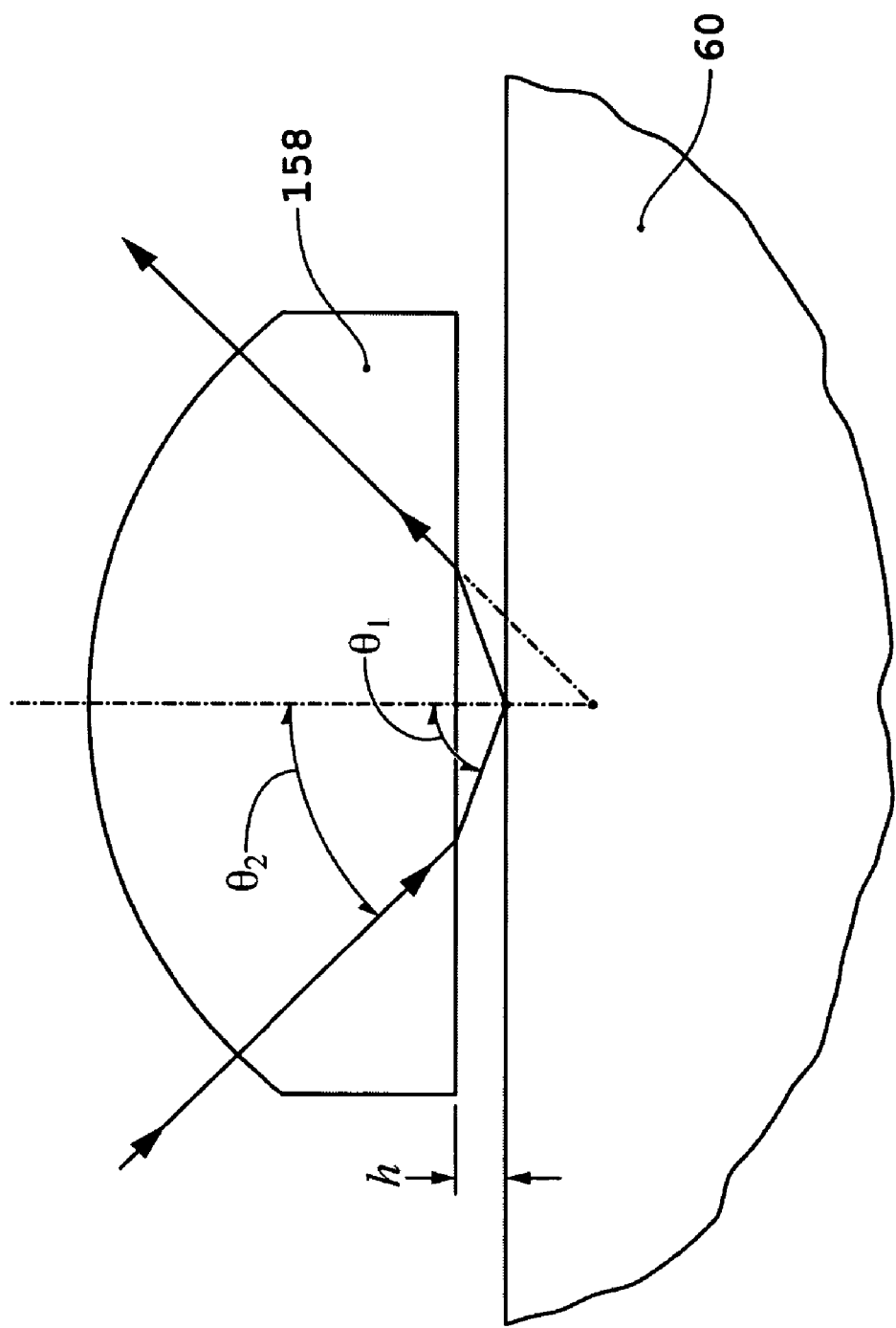
FIG. 2d is a schematic diagram of a section of a catadioptric imaging system located near a measurement object.
Figure 2E:
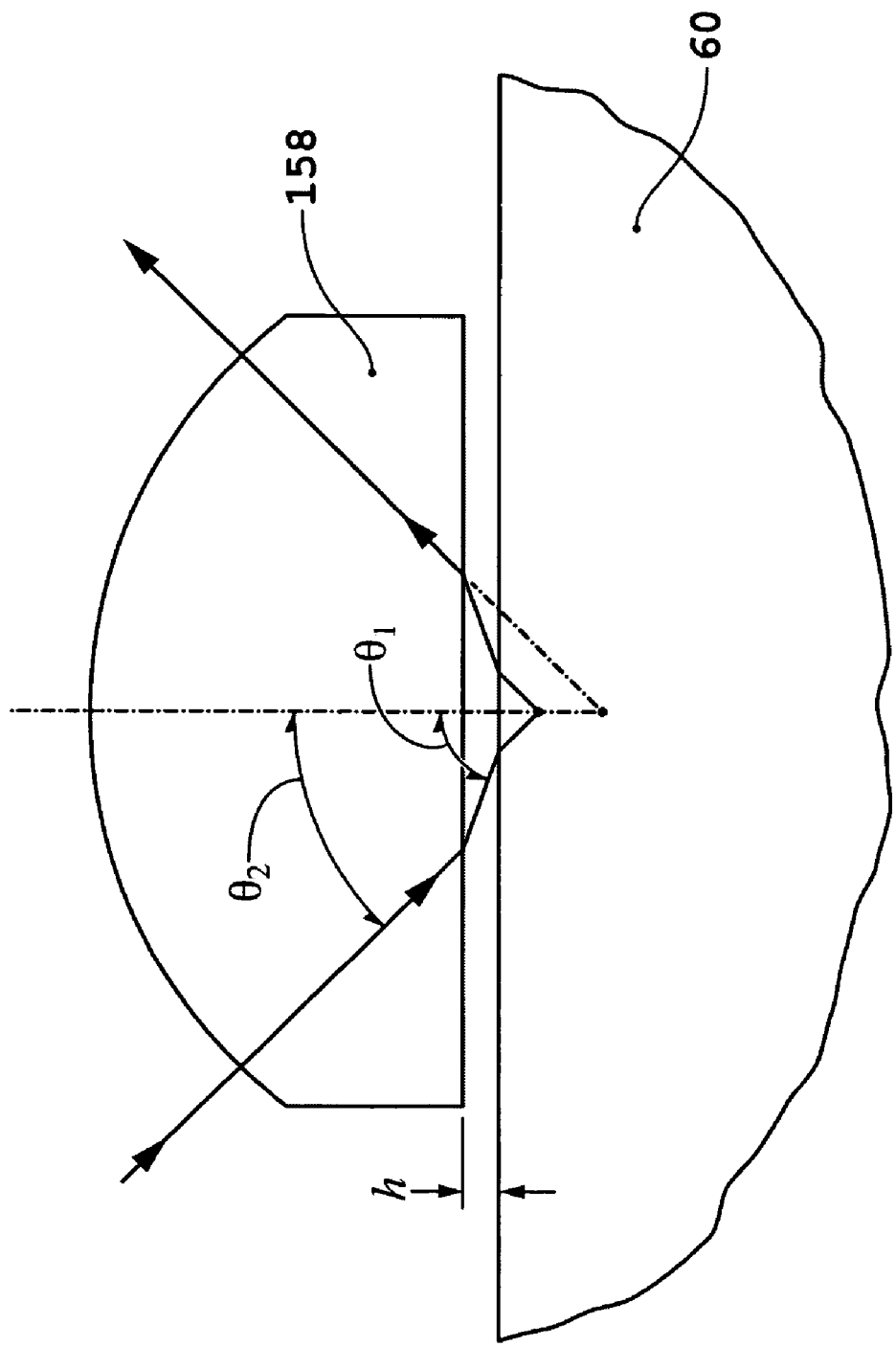
FIG. 2e is a schematic diagram of a section of a catadioptric imaging system located near a measurement object and imaging an interior section of the measurement object.
Figure 2F:
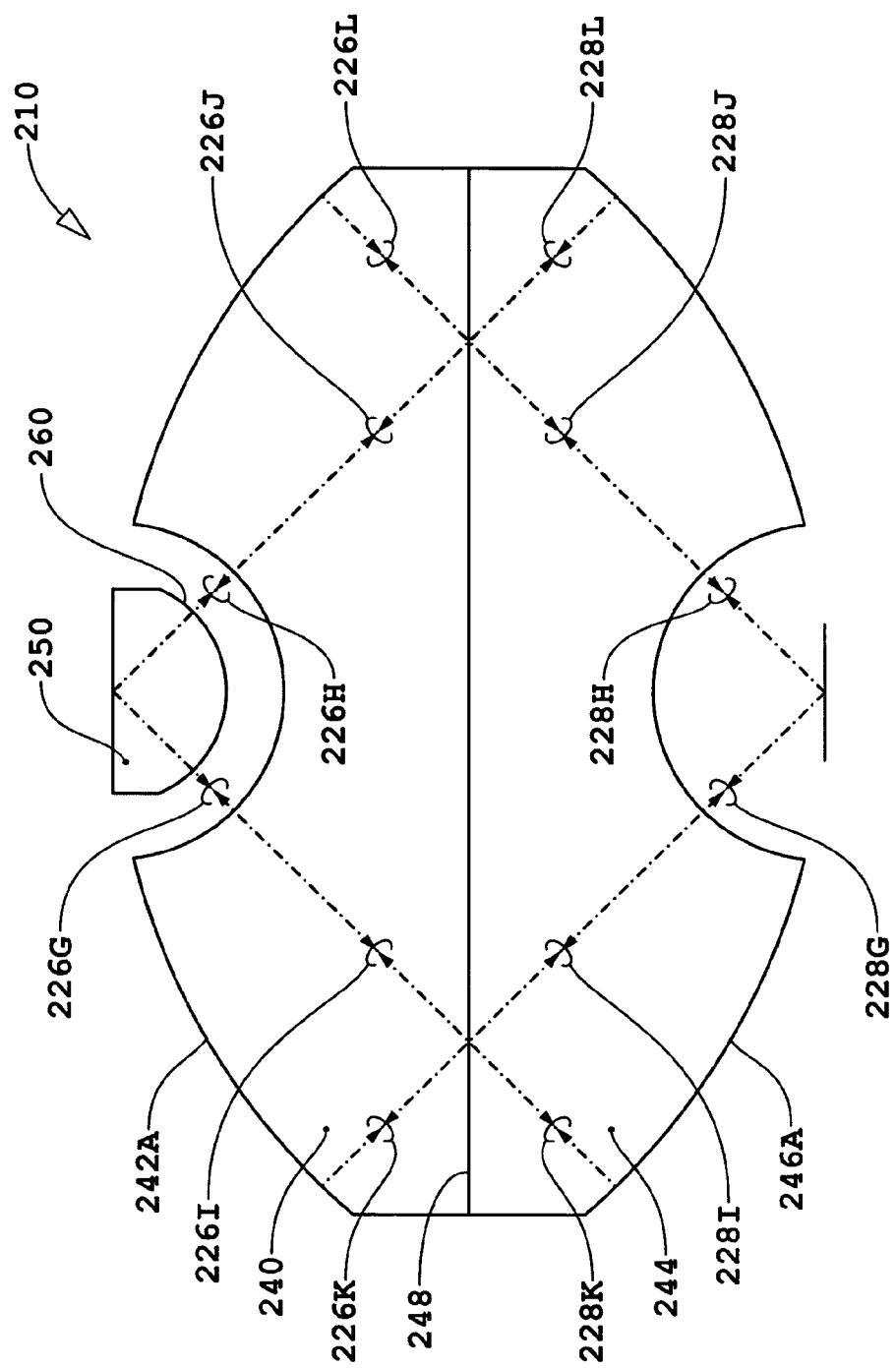
FIG. 2f is a schematic diagram an astigmatic catadioptric imaging system.

Another form of anastigmat catadioptric imaging system that may be used for catadioptric and catoptric imaging system 100 is the catadioptric imaging system such as described in cited U.S. Provisional Patent Application No. 60/460,129 (ZI-51) and shown schematically in FIG. 2f. The catadioptric imaging system shown in FIG. 2f comprises the same elements as the astigmatic catadioptric imaging system shown in FIG. 2c except for the omission of element 258. The sagittal field of catadioptric imaging system 210 shown in FIG. 2f is a flat field and the tangential field is also a flat field for a certain object field when the Petzval sum is zero, i.e., $$\left(\frac{1}{n_1} - \frac{1}{n_2}\right)\frac{1}{r_1} + 2\sum_{j=2}^{p-1}\left(\frac{1}{n_j} - \frac{1}{n_{j+1}}\right)\frac{1}{r_j} + \frac{1}{n_p}\frac{2}{r_p} = 0 \quad (9)$$

where $r_1$ corresponds to the radius of curvature of surface 260. An example of a set of respective radii of curvature for an anastigmat design for at λ=250 nm using fused silica comprises the same radii listed in Table 3 for $r_2$ and $r_3$ and ½ of the value listed for $r_1$.

The location of the object plane of catadioptric imaging system 210 is outside of plano convex lens 158 and on the surface of substrate 60 which is shown diagrammatically in FIG. 2d. The separation of the plane surface of plano convex lens 158 and the surface of substrate 60 is h. The object plane of catadioptric imaging system 210 may also be located in the interior of substrate 60 which is shown diagrammatically in FIG. 2e. When used in an end use application where the resolution of catadioptric imaging system 210 is restricted to a Δθ such as described with respect to Equation (6), the spherical aberration introduced by transmission through plane surfaces shown in FIGS. 2d and 2e generally will not impact on the performance of the imaging system 210.

An advantage of the catadioptric imaging system 210 is that as a consequence of the spherical aberration introduced by transmission through plane surfaces, the effective angle of incidence $\theta_1$ can be scanned by introducing a scan in h.

For those end use applications where compensation is required for the spherical aberration introduced by transmission through plane surfaces, procedures may be use such as described in commonly owned U.S. Provisional Application No. 60/444,707 (ZI-44) and U.S. patent application Ser. No. 10/771,785 (ZI-44) of which both are entitled "Compensation for Effects of Mismatch in Indices of Refraction at a Substrate-Medium Interface in Confocal and Interferometric Confocal Microscopy," both are to Henry A. Hill, and the contents of both are herein incorporated in their entirety by reference.

Figure 1D:
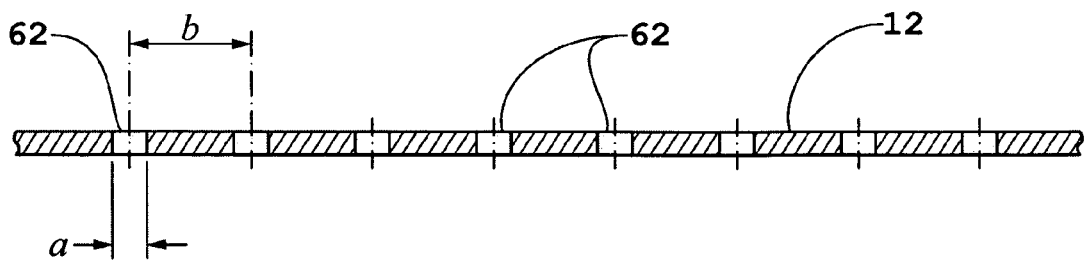
FIG. 1d is a diagram of a pinhole array beam-splitter.

The description of imaging system 100 is continued with reference to FIG. 1c. Lens sections 40 and 44 are sections, e.g., pie sections, of lens 240 and 244 shown in FIG. 2a. Lens elements 250, 256, 254, and 258 in FIG. 1c are the same elements lens elements 250, 256, 254, and 258 in FIG. 2a. Convex lens 52 has a center of curvature the same as the center of curvature of convex lens 250. Convex lenses 250 and 52 are bonded together with pinhole array beam-splitter 12 in between. Pinhole array beam-splitter 12 is shown in FIG. 1d. The pattern of pinholes in pinhole array beam-splitter is chosen so that the image of pinhole array beam-splitter 12 on detector 70 to match the pixel pattern of detector 70. An example of a pattern is a two dimensional array of equally spaced pinholes in two orthogonal directions. The pinholes may comprise circular apertures, rectangular apertures, or combinations thereof such as described in commonly owned U.S. patent application Ser. No. 09/917,402 (ZI-15) entitled "Multiple-Source Arrays for Confocal and Near-field Microscopy" by Henry A. Hill and Kyle Ferrio of which the contents thereof are incorporated herein in their entirety by reference. The pinholes may also comprise microgratings such as described in cited U.S. Provisional Patent Application No. 60/459,425 and U.S. patent application Ser. No. 10/816,180, (ZI-50) filed Apr. 1, 2004 and entitled "Apparatus and Method for Joint Measurement Of Fields Of Scattered/Reflected Or Transmitted Orthogonally Polarized Beams By An Object In Interferometry". A nonlimiting example of a pinhole array for pinhole array beam-splitter 12 is shown in FIG. 1d having a spacing between pinholes of b with aperture size a.

With reference to FIGS. 1b and 1c, a first portion of input beam 24 is reflected by non-polarizing beam-splitter 54A and incident on pinhole array beam-splitter 12 after reflection by mirrors 54B and 54C. The angle of incidence of the reference beam at pinhole array beam-splitter 12 is selected to correspond to $\theta_D$ (see Equation (3) and related discussion) in the plane of FIG. 1c. The reference beam may alternatively be incident on pinhole array beam-splitter 12 from the opposite side with an angle of incidence equal to $\theta_D$ in the plane of FIG. 1c. The direction of propagation of the reference beam incident from the opposite side is the mirror image about the surface of pinhole array beam-splitter 12 of the direction of propagation of the reference beam shown in FIG. 1c. A portion of the beam reflected by beam-splitter 54A and incident on pinhole array beam-splitter 12 is reflected as reference beam components of output beam 32A and 32B (see FIG. 1b).

A general property of various embodiments of the present invention is that the integrated interference cross-term between the reference beam and the respective return measurement beam across the spot by the detector 70 will have a peak in detection sensitivity for the reflected/scattered return measurement beam components of beams 28C that have an angle of diffraction corresponding to $\theta_D$. By the selection of the angle of incidence of the reference beam at pinhole array beam-splitter 12 to correspond to $\theta_D$, the reflected/scattered return measurement beam components of beams 28C across the spot on beam-splitter 12 remains in phase with the reference beam. As a consequence, the interference cross-term between the reference beam and the respective return measurement beam across the spot comprises a constant term and an oscillatory term. In this case, the interference cross-term integrates across the spot to a meaningful non-zero value proportional to the constant term. Whereas the projection of the spatial wavelength onto beam splitter 12 for the other diffraction angles of the return measurement beam is not equal to the projection of the wavelength of the reference beam onto beam-splitter 12 so that the return measurement beam components of beams 28C across the spot on beam-splitter 12 do not remain in phase with the reference beam. Accordingly, the interference cross-term for those diffraction directions oscillates across the spot comprising two oscillatory terms and therefore their contributions integrate to zero or reduced values.

Another general property of various embodiments of the present invention is that the since the reference beam is generated with the angle of incidence at pinhole array beam-splitter 12 selected to correspond to $\theta_D$, the phases of conjugated quadratures corresponding to the interference cross-term between the reference beam and the reflected/scattered return measurement beam components of beams 28C in the electrical interference signal 72 generated by detection of mixed output beams by detector 70 is $\zeta_x$ and $\zeta_y$ (see Equations (1) and (2) and associated description) with no dependences on either x or y. This is an important feature since the phase represented in conjugated quadratures is a function only of the reflecting properties and location of the defect and/or artifact in addition to a fixed offset error in the interferometric metrology system. A corollary statement is that the accuracy to which the location of a defect and/or artifact on or in substrate being imaged can be measured is not affected by displacements of a pinhole corresponding to a detector or of a detector pixel used in measuring the respective conjugated quadratures other than contributing to a phase redundancy mod $2\pi$.

A second portion of beam 24 is transmitted by beam-splitter 54A as measurement beam 24A after reflection by mirror 54D. Measurement beam 24A is incident on substrate 60 and a portion thereof is reflected and/or scattered as return measurement beam components of beams 28C. The angle of incidence of the measurement beam at substrate 60 is selected to correspond to $\theta_1$ (see Equation (3) and related discussion). Return measurement beam components of beam 28C are imaged by catadioptric imaging system 100 to pinhole array beam-splitter 12 and a portion thereof is transmitted as return measurement beam components of output beams 32A and 32B.

The next step is the imaging of output beams 32A and 32B by imaging system 110 to an array of spots that coincide with the pixels of a multi-pixel detector such as a CCD to generate an array of electrical interference signals 72. The array of electrical interference signals is transmitted to signal processor and controller 80 for subsequent processing.

Conjugated quadratures of fields of the return measurement beam are obtained by single-homodyne detection in the first embodiment of the present invention. For the single-homodyne detection, a set of four measurements of electrical interference signals 72 is made. For each of the four measurements of the electrical interference signals 72, a known phase shift is introduced between the reference beam component and respective return measurement beam component of output beams 32A and 32B. A nonlimiting example of a known set of phase shifts comprise 0, $\pi/4$, $\pi/2$, and $3\pi/2$ radians.

Input beam 24 comprises in the first embodiment one frequency component. The phase shifts are generated in the first embodiment by shifting the frequency of the input beam 24 between known frequency values. There is a difference in optical path length between the reference beam components and the respective return beam components of output beams 32A and 32B and as a consequence, a change in frequency of input beam 24 will generate a corresponding phase shift between the reference beam components and the respective return beam components of output beams 32A and 32B.

For an optical path difference L between the reference beam components and the respective return measurement beam components of output beams 32A and 32B, there will be for a frequency shift $\Delta f$ a corresponding phase shift $\phi$ where $$\varphi = 2\pi L\left(\frac{\Delta f}{c}\right) \quad (10)$$

and c is the free space speed of light. Note that L is not a physical path length difference and depends for example on the average index of refraction of the measurement beam and the return measurement beam paths. For an example of a phase shift $\phi=\pi$, $3\pi$, $5\pi$, ... and a value of L=0.25 m, the corresponding frequency shift $\Delta f$=600 MHz, 1.8 GHz, 3.0 GHz, ....

The frequency of input beam 24 is determined by beam-conditioner 22 according to control signal 74 generated by electronic processor and controller 80. Source 18 of input beam 20, such as a laser, can be any of a variety of single frequency lasers.

Two different modes of operation are described for the acquisition of the four electrical interference signal values. The first mode to be described is a step and stare mode wherein substrate 60 is stepped between fixed locations for which image information is desired. The second mode is a scanning mode. In the step and stare mode for generating a one-, a two-, or a three-dimensional image of substrate 60, substrate 60 is translated by stage 90 wherein substrate 60 is mounted on wafer chuck 84 with wafer chuck 84 mounted on stage 90. The position of stage 90 is controlled by transducer 82 according to servo control signal 78 from electronic processor and controller 80. The position of stage 90 is measured with respect to a reference system by metrology system 88 and position information acquired by metrology system 88 is transmitted to electronic processor and controller 80 to generate an error signal for use in the position control of stage 90. The reference system may correspond to the reference frame of a lithography tool used for writing to a wafer or an inspection tool for lithography masks or reticles. Metrology system 88 may comprise for example linear displacement and angular displacement interferometers and cap gauges.

Electronic processor and controller 80 translates stage 90 to a desired position and then acquires the set of four electrical interference signal values corresponding to the set of four phase shifts 0, $\pi/4$, $\pi/2$, and $3\pi/2$. After the acquisition of the sequence of four electrical interference signal values, electronic processor and controller 80 repeats the procedure for the next desired position of stage 90. The elevation and angular orientation of substrate 60 is controlled by transducers 86A and 86B.

The second of the two modes for the acquisition of the electrical interference signal values is next described wherein the electrical interference signal values are obtained with the position of stage 90 scanned in one or more directions. In the scanning mode, source 18 is pulsed at times controlled by signal 92 from signal processor and controller 80. Source 18 is pulsed at times corresponding to the registration of the conjugate image of pinholes of pinhole array beam-splitter 12 with positions on and/or in substrate 60 for which image information is desired.

There will be a restriction on the duration or "pulse width" of a beam pulse $\tau_{p1}$ produced by source 18 as a result of the continuous scanning used in the scanning mode of the first embodiment. Pulse width $\tau_{p1}$ will be a parameter that in part controls the limiting value for spatial resolution in the direction of a scan to a lower bound of $$\tau_{p1} v, \quad (11)$$

where v is the scan speed. For example, with a value of $\tau_{p1}=50$ nsec and a scan speed of v=0.20 m/sec, the limiting value of the spatial resolution $\tau_{p1} v$ in the direction of scan will be $$\tau_{p1} v = 10 \text{ nm}. \quad (12)$$

The frequency of input beam 24 is controlled by signal 74 from electronic processor and controller 80 to correspond to a frequency of a set of four frequencies that will yield the desired phase shift of the set of four phase shifts between the reference and return measurement beam components of output beams 32A and 32B. In the first mode for the acquisition of the electrical interference signal values, each of the sets of four electrical interference signal values corresponding to the set of four phase shift values are generated by a single pixel of detector 70. In the second mode for the acquisition of the electrical interference signal values, the set of four electrical interference signal values corresponding to the set of four phase shift values are generated by a conjugate set of four different pixels of detector 70. Thus in the second mode of acquisition, the differences in pixel efficiency and the differences in sizes of pinholes in pinhole array beam-splitter 12 need to be compensated in the signal processing by electronic processor and controller 80 to obtain conjugated quadratures of fields of return measurement beam components.

The advantage of the second mode is that the electrical interference signal values are acquired in a scanning mode which increases through put of the interferometric confocal microscopy system of the first embodiment.

The description beam-conditioner 22 is the same as the description given for the two frequency generator and frequency-shifter described in cited U.S. Provisional Application No 60/442,858 (ZI-47) and U.S. patent application Ser. No. 10/765,368, filed Jan. 27, 2004 (ZI-47) and entitled "Apparatus and Method for Joint Measurements of Conjugated Quadratures of Fields of Reflected/Scattered Beams by an Object in Interferometry."

Figure 1E:
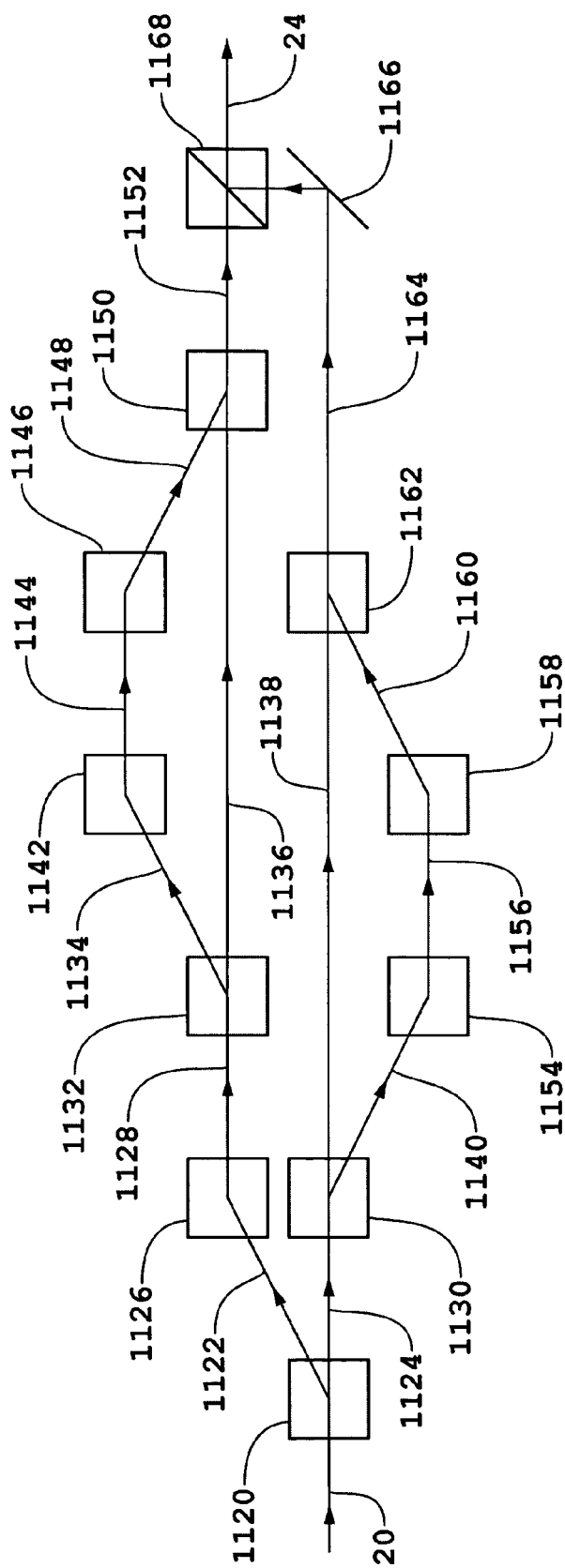
FIG. 1e is a schematic diagram of a beam-conditioner configured as a two-frequency generator and a frequency-shifter.

Reference is made to FIG. 1e where beam-conditioner 22 is first described generally as a two-frequency generator and a frequency-shifter. Beam-conditioner 22 may be operated to generate a beam 24 that has either a single frequency-shifted component or two frequency-shifted components. Beam-conditioner 22 is operated in the single frequency-shifted mode for the first embodiment.

Beam-conditioner 22 comprises acousto-optic modulators 1120, 1126, 1130, 1132, 1142, 1146, 1150, 1154, 1058, and 1062; beam-splitter 1168; and mirror 1166. Input beam 20 is incident on acousto-optic modulator 1120 with a plane of polarization parallel to the plane of FIG. 1e. A first portion of beam 20 is diffracted by acousto-optic modulator 1120 as beam 1122 and then by acousto-optic modulator 1126 as beam 1128 having a polarization parallel to the plane of FIG. 1e. A second portion of beam 20 is transmitted as a non-diffracted beam 1124 having a plane of polarization parallel to the plane of FIG. 1e.

For beam-conditioner 22 operated to generate the single frequency-shifted component for beam 24, the acoustic power to acousto-optic modulator 1120 is switched between two states. One state is the off state where the amplitude of diffracted beam 1122 in zero and in the on state, the amplitude of non-diffracted beam 1124 is nominally zero. The on or off states of acousto-optic modulator 1120 is controlled by signal 74 generated by electronic processor and controller 80

Acousto-optic modulators 1120 and 1126 may be of either the non-isotropic Bragg diffraction type or of the isotropic Bragg diffraction type. The frequency shifts introduced by acousto-optic modulators 1120 and 1126 are of the same sign and equal to ½ of a frequency shift $\Delta f$ that will generate in interferometer 10 a $\pi/2$ phase difference between a reference beam and a measurement beam that have a difference in frequency equal to frequency shift $\Delta f$. The direction of propagation of beam 1128 is parallel to the direction of propagation of beam 1124.

Continuing with FIG. 1e, beam 1128 is incident on acousto-optic modulator 1132 and is either diffracted by acousto-optic modulator 1132 as beam 1134 or transmitted by acousto-optic modulator 1132 as beam 1136 according to control signal 74 from electronic processor and controller 80. When beam 1134 is generated, beam 1134 is diffracted by acousto-optic modulators 1142, 1146, and 1150 as a frequency shifted beam component of beam 1152. The frequency shifts introduced by acousto-optic modulators 1132, 1142, 1146, and 1150 are all in the same direction and equal in magnitude to $\Delta f/2$. Thus the net frequency shift introduced by acousto-optic modulators 1132, 1142, 1146, and 1150 is $\pm 2\Delta f$. The net frequency shift introduced by acousto-optic modulators 1120, 1126, 1132, 1142, 1146, and 1150 is $\Delta f \pm 2\Delta f$ that in turn will generate a respective relative phase shift of $\pi/2 \pm \pi$ between the respective reference and measurement beams in interferometer 10.

When beam 1136 is generated, beam 1136 is transmitted by acousto-optic modulator 1150 according to control signal 74 from electronic processor and controller 80 as a non-frequency shifted beam component of beam 1152. The frequency shift introduced by acousto-optic modulators 1120, 1126, 1132, and 1150 is Δf which will generate a respective relative phase shift of π/2 between the respective reference and measurement beams in interferometer 10.

Beam 1124 is incident on acousto-optic modulator 1130 and is either diffracted by acousto-optic modulator 1130 as beam 1140 or transmitted by acousto-optic modulator 1130 as beam 1138 according to control signal 74 from electronic processor and controller 80. When beam 1140 is generated, beam 1140 is diffracted by acousto-optic modulators 1154, 1158, and 1162 as a frequency-shifted beam component of beam 1164. The frequency shifts introduced by acousto-optic modulators 1130, 1154, 1158, and 1162 are all in the same direction and equal to ±Δf/2. Thus the net frequency shift introduced by acousto-optic modulators 1130, 1154, 1158, and 1162 is ±2Δf and will generate a relative phase shift of ±π between the respective reference and measurement beams in interferometer 10. The net frequency shift introduced by acousto-optic modulators 1120, 1130, 1154, 1158, and 1162 is ±2Δf and will generate a respective relative phase shift of ±π between the respective reference and measurement beams in interferometer 10.

When beam 1138 is generated, beam 1138 is transmitted as a non-frequency shifted beam component of beam 1164. The corresponding frequency shift introduced by acousto-optic modulators 1120, 1130, and 1162 is 0 and will generate a respective relative phase shift of 0 between the respective reference and measurement beams in interferometer 10.

Beams 1152 and 1164 may be used directly as input beam 24 when an embodiment requires spatially separated reference and measurement beams for an input beam. When an embodiment of the present invention requires coextensive reference and measurement beams as an input beam, beam 1152 and 1164 are next combined by beam-splitter 1168 to form beam 24. Acousto-optic modulators 1120, 1126, 1130, 1132, 1142, 1146, 1150, 1154, 1158, and 1162 may be either of the non-isotropic Bragg diffraction type or of the isotropic Bragg diffraction type. Beams 1152 and 1164 are both polarized in the plane of FIG. 1e for either non-isotropic Bragg diffraction type or of the isotropic Bragg diffraction type and beam-splitter 1168 is of the non-polarizing type.

In the first embodiment of the present invention, the processing of the measured arrays of sets of four measured electrical interference signal values for the determination of conjugated quadratures of fields of return measurement beams is described herein as a special case of the bi-homodyne detection method and is also described for example in cited U.S. Pat. No. 6,445,453 (ZI-14).

Referring to the bi-homodyne detection method such as described in cited U.S. Provisional Patent Application No. 60/442,858 (ZI-47) and cited U.S. patent application Ser. No. 10/765,368, filed Jan. 27, 2004 (ZI-47) entitled "Apparatus and Method for Joint Measurements of Conjugated Quadratures of Fields of Reflected/Scattered and Transmitted Beams by an Object in Interferometry" wherein conjugated quadratures are obtained jointly, a set of four electrical interference signal values is obtained for each spot on and/or in substrate 60 being imaged. The set of four electrical interference signal values $S_j$, j=1,2, 3,4 used for obtaining conjugated quadratures of fields for a single a spot on and/or in a substrate being imaged is represented for the bi-homodyne detection within a scale factor by the formula $$S_j = P_j \sum_{m=1}^{2} \begin{Bmatrix} \xi_j^2|A_m|^2 + \zeta_j^2|B_m|^2 + \eta_j^2|C_m|^2 + \\ \zeta_j\eta_j 2|B_m||C_m|\cos\varphi_{B_m C_m}\varepsilon_{m,j} + \\ \xi_j\zeta_j 2|A_m||B_m|\cos\varphi_{A_m B_m}\varepsilon_{m,j} + \\ \varepsilon_{m,j}\xi_j\eta_j[1-(-1)^m]|A_m||C_m|\cos\varphi_{A_m C_m} + \\ \varepsilon_{m,j}\xi_j\eta_j[1+(-1)^m]|A_m||C_m|\sin\varphi_{A_m C_m} \end{Bmatrix} \quad (1)$$

where coefficient $A_m$ represents the amplitude of the reference beam corresponding to the frequency component of the input beam 24 that has index m; coefficient $B_m$ represents the amplitude of the background beam corresponding to reference beam $A_m$; coefficient $C_m$ represents the amplitude of the return measurement beam corresponding to reference beam $A_m$; $P_j$ represents the integrated intensity of the first frequency component of the input beam 24 pulse j of a sequence of 4 pulses; and an example set of values for $\varepsilon_{m,j}$ are listed in Table 4. There are other set of values for $\varepsilon_{m,j}$ that may be used in embodiments of the present invention wherein the other set of values for $\varepsilon_{m,j}$ satisfy the conditions set out in subsequent Equations (14) and (15) herein.

The change in the values of $\varepsilon_{m,j}$ from 1 to −1 or from −1 to 1 corresponds to changes in relative phases of respective reference and measurement beams. The coefficients $\xi_j$, $\zeta_j$, and $\eta_j$ represent effects of variations in properties of a conjugate set of four pinholes such as size and shape if used in the generation of the spot on and/or in substrate 60 and the sensitivities of a conjugate set of four detector pixels corresponding to the spot on and/or in substrate 60 for the reference, background, and the return measurement beam, respectively. In the single-frequency single-homodyne detection operating in a non-scanning mode, the conjugate set of pinholes corresponds to a single pinhole and the conjugate set of four pixels corresponds to a single pixel. The conjugate set of four pinholes comprise pinholes of pinhole array beam-splitter 12 that are conjugate to a spot in or on the substrate being imaged at different times during the scan.

TABLE 4

| | $\varepsilon_{m,j}$ | |
|---|---|---|
| | m | |
| j | 1 | 2 |
| 1 | 1 | 1 |
| 2 | 1 | −1 |
| 3 | −1 | −1 |
| 4 | −1 | 1 |

The relationships $\cos\phi_{A_2C_2}=\sin\phi_{A_1C_1}$ and $\cos\phi_{A_4C_4}=\sin\phi_{A_3C_3}$ have been used in deriving Equation (13) without departing from either the scope or spirit of the present invention since $\cos\phi_{A_2C_2}=\pm\sin\phi_{A_1C_1}$ and $\cos\phi_{A_4C_4}=\pm\sin\phi_{A_3C_3}$ by control of the relative phase shifts between corresponding reference and return measurement beam components in beam 32.

It has also been assumed in Equation (13) that the ratios $|A_2|/|A_1|$ and $|A_4|/|A_3|$ are not dependent on j or on the value of $P_j$. In order to simplify the representation of $S_j$ so as to project the important features without departing from either the scope or spirit of the present invention, it is also assumed in Equation (13) that the corresponding ratios of the amplitudes of the return measurement beams are not dependent on j or on the value of $P_j$. However, the ratios $|C_2|/|C_1|$ and $|C_4|/|C_3|$ will be different from the ratio $|A_2|/|A_1|$ and $|A_4|/|A_3|$, respectively, the ratios of the amplitudes of the measurement beam components corresponding to $A_2$ and $A_1$ are different from the ratio $|A_2|/|A_1|$ and corresponding to $A_4$ and $A_3$ are different from the ratio $|A_4|/|A_3|$.

The change in phases $\phi_{A_mB_m\epsilon_{m,j}}$ for a change in $\epsilon_{m,j}$ may be different from $\pi$ for embodiments where phase shifts are introduced between the arrays of reference and measurement beams by changing the frequency of an input beam component. It may be of value in evaluating the effects of the background beams to note that the factor $\cos \phi_{B_mC_m\epsilon_{m,j}}$ may be written as $$\cos[\varphi_{A_mC_m} + (\varphi_{B_mC_m\epsilon_{m,j}} - \varphi_{A_mC_m})]$$

where the phase difference $(\phi_{B_mC_m\epsilon_{m,j}} - \phi_{A_mC_m})$ is the same as the measured phase $\phi_{A_mB_m\epsilon_{m,j}}$.

It is evident from inspection of Equation (13) that the components of conjugated quadratures $\epsilon_{m,j}|C_m|\cos \phi_{A_mC_m}$ and $\epsilon_{m,j}|C_m|\sin \phi_{A_mC_m}$ in Equation (13) are functions that have mean values of zero since $$\sum_{j=1}^{4} \epsilon_{m,j} = 0, \quad m = 1, 2. \tag{14}$$

Another important property is that the conjugated quadratures $\epsilon_{m,j}|C_m|\cos \phi_{A_mC_m}$ and $\epsilon_{m',j}|C_m|\sin \phi_{A_mC_m}$, are orthogonal over the range of m=1,2 for m≠m' since $\epsilon_{m,j}$ and $\epsilon_{m',j}$ are orthogonal over the range of j=1, 2, 3, 4, i.e., $$\sum_{j=1}^{4} \epsilon_{m,j} \epsilon'_{m',j} = 4\delta'_{m,m'} \tag{15}$$

where $\delta_{m,m'}$ is the Kronecker delta defined by $\delta_{m,m'} = 1$ for m=m', $\delta_{m,m'} = 0$ for m≠m'. (16)

Information about conjugated quadratures $|C_m|\cos \phi_{A_mC_m}$ and $|C_m|\sin \phi_{A_mC_m}$ is obtained using a digital filter $F_m(S_j)$ on signals $S_j$ that are based on the orthogonality properties of the $\epsilon_{m,j}$ as represented by Equation (15). The definition of $F_m(S_j)$ and the output of digital filter $F(S_j)$ are $$F_m(S_j) = \sum_{j=1}^{4} \epsilon_{m,j} \frac{S_j}{P_j \xi_j'^2} = \sum_{m'=1}^{2} |A_m'|^2 \sum_{j=1}^{4} \epsilon_{m,j} \left(\frac{P_j}{P_j'}\right)\left(\frac{\xi_j^2}{\xi_j'^2}\right) + \tag{17}$$

$$\sum_{m'=1}^{2} |B_m'|^2 \sum_{j=1}^{4} \epsilon_{m,j} \left(\frac{P_j}{P_j'}\right)\left(\frac{\zeta_j^2}{\xi_j'^2}\right) +$$

$$\sum_{m'=1}^{2} |C_m'|^2 \sum_{j=1}^{4} \epsilon_{m,j} \left(\frac{P_j}{P_j'}\right)\left(\frac{\eta_j^2}{\xi_j'^2}\right) +$$

-continued $$[1-(-1)^m]|A_m||C_m|\cos\varphi_{A_mC_m}\sum_{j=1}^{4}\left(\frac{P_j}{P_j'}\right)\left(\frac{\xi_j\eta_j}{\xi_j'^2}\right)\sum_{m'=1}^{2}\epsilon_{m,j}\epsilon'_{m,j} +$$

$$[1+(-1)^m]|A_m||C_m|\sin\varphi_{A_mC_m}\sum_{j=1}^{4}\left(\frac{P_j}{P_j'}\right)\left(\frac{\xi_j\eta_j}{\xi_j'^2}\right)\sum_{m'=1}^{2}\epsilon_{m,j}\epsilon'_{m,j} +$$

$$2\sum_{m'=1}^{2}|A_m'||B_m'|\sum_{j=1}^{4}\epsilon_{m,j}\left(\frac{P_j}{P_j'}\right)\left(\frac{\xi_j\zeta_j}{\xi_j'^2}\right)\cos\varphi_{A_m'B_m'\epsilon'_{m,j}} +$$

$$2\sum_{m'=1}^{2}|B_m'||C_m'|\sum_{j=1}^{4}\epsilon_{m,j}\left(\frac{P_j}{P_j'}\right)\left(\frac{\zeta_j\eta_j}{\xi_j'^2}\right)\cos\varphi_{B_m'C_m'\epsilon'_{m,j}}.$$

where $\xi_j'$ and $P_j'$ are values used in the digital filters to represent $\xi_j$ and $P_j$, respectively.

The conjugated quadratures $|C_m|\cos \phi_{A_mC_m}$ and $|C_m|\sin \phi_{A_mC_m}$ correspond to the interference cross-term between the reference beam and the reflected/scattered return measurement beam components of beams 28C in the electrical interference signal 72 generated by detection of mixed output beams by detector 70. The phase of the conjugated quadratures $|C_m|\cos \phi_{A_mC_m}$ and $|C_m|\sin \phi_{A_mC_m}$, i.e., $\phi_{A_mC_m}$, relates to $\zeta_x$ and $\zeta_y$ (see Equations (1) and (2) and associated description).

The parameters $$\left[\left(\frac{|A_2|}{|A_1|}\right)\left(\frac{|C_2|}{|C_1|}\right)\right], \tag{18}$$

$$\left[\left(\frac{|A_4|}{|A_3|}\right)\left(\frac{|C_4|}{|C_3|}\right)\right] \tag{19}$$

need to be determined in order complete the determination of a conjugated quadratures. The parameters given in Equations (18) and (19) can be measured for example by introducing $\pi/2$ phase shifts into the relative phase of the reference beam and the measurement beam and repeating the measurement for the conjugated quadratures. The ratios of the amplitudes of the conjugated quadratures corresponding to $(\sin \phi_{A_1C_1}/\cos \phi_{A_1C_1})$ and $(\sin \phi_{A_3C_3}/\cos \phi_{A_3C_3})$ from the first measurement divided by the ratios of the amplitudes of the conjugated quadratures corresponding to $(\sin \phi_{A_1C_1}/\cos \phi_{A_1C_1})$ and $(\sin \phi_{A_3C_3}/\cos \phi_{A_3C_3})$ respectively, from the second measurement are equal to $$\left[\left(\frac{|A_2|}{|A_1|}\right)\left(\frac{|C_2|}{|C_1|}\right)\right]^2, \tag{20}$$

$$\left[\left(\frac{|A_4|}{|A_3|}\right)\left(\frac{|C_4|}{|C_3|}\right)\right]^2, \tag{21}$$

respectively.

Note that certain of the factors in Equation (17) have nominal values of 4 within a scale factor, e.g., have nominal values of either 0 or 4, e.g., $$\sum_{j=1}^{4}\left(\frac{P_j}{P'_j}\right)\left(\frac{\xi_j\eta_j}{\xi_j'^2}\right)\sum_{m'=1}^{2}\varepsilon_{m,j}\varepsilon'_{m,j} \cong \sum_{j=1}^{4}\left(\frac{P_j}{P'_j}\right)\left(\frac{\xi_j\eta_j}{\xi_j'^2}\right)\delta'_{m,m} \cong 4\delta'_{m,m} \qquad (22)$$

where $\delta_{m,m'}$ is the Kronecker delta defined by Equation (16). The scale factors corresponds to the average value for the ratio of $(\xi'_j)^2/(\xi_j\eta_j)$ assuming that the average values of $P_j/P'_j \cong 1$.

Certain other of the factors in Equation (17) have nominal values of zero, e.g., $$\sum_{j=1}^{4}\varepsilon_{m,j}\left(\frac{P_j}{P'_j}\right)\left(\frac{\xi_j^2}{\xi_j'^2}\right) \cong 0, \quad \sum_{j=1}^{4}\varepsilon_{m,j}\left(\frac{P_j}{P'_j}\right)\left(\frac{\zeta_j^2}{\xi_j'^2}\right) \cong 0, \qquad (23)$$

$$\sum_{j=1}^{4}\varepsilon_{m,j}\left(\frac{P_j}{P'_j}\right)\left(\frac{\eta_j^2}{\xi_j'^2}\right) \cong 0.$$

The remaining factors, $$\sum_{j=1}^{4}\varepsilon_{m,j}\left(\frac{P_j}{P'_j}\right)\left(\frac{\xi_j\zeta_j}{\xi_j'^2}\right)\cos\varphi_{A'_m B'_m \varepsilon'_{m,j}}, \qquad (24)$$

$$\sum_{j=1}^{4}\varepsilon_{m,j}\left(\frac{P_j}{P'_j}\right)\left(\frac{\zeta_j\eta_j}{\xi_j'^2}\right)\cos\varphi_{B'_m C'_m \varepsilon'_{m,j}}$$

will have nominal magnitudes ranging from of approximately zero to approximately 4 times a cosine factor and either the average value of factor $(P_j/P'_j)(\xi_j\zeta_j/\xi_j'^2)$ or $(P_j/P'_j)(\zeta_j\eta_j/\xi_j'^2)$ depending on the properties respective phases. For portion of the background with phases that do not track to a first approximation the phases of the respective measurement beams, the magnitudes of all of the terms listed in the Equation (24) will be approximately zero. For the portion of the background with phases that do track to a first approximation the phases of the respective measurement beams, the magnitudes of the terms listed in Equation (24) will be approximately 4 times a cosine factor and either the average value of factor $(P_j/P'_j)(\xi_j\zeta_j/\xi_j'^2)$ or $(P_j/P'_j)(\zeta_j\eta_j/\xi_j'^2)$.

The two potentially largest terms in Equations (17) are generally the terms that have the factors $$\sum_{m'=1}^{4}|A'_m|^2 \text{ and } \sum_{m'=1}^{4}|B'_m|^2.$$

However, the corresponding terms are substantially eliminated in embodiments using the bi-homodyne detection method as result of the properties of the factors listed in Equation (23).

The largest contribution from effects of background is represented by the contribution to the interference term between the reference beam and the portion of the background beam generated by the measurement beam 30A. This portion of the effect of the background can be measured in embodiments of the bi-homodyne detection method by measuring the corresponding conjugated quadratures of the portion of the background with the return measurement beam component of beam 32 set equal to zero, i.e., measuring the respective electrical interference signals $S_j$ with substrate 60 removed and with either $|A_2|=0$ or $|A_1|=0$ and visa versa and with either $|A_4|=0$ or $|A_3|=0$ and visa versa. The measured conjugated quadratures of the portion of the effect of the background can than be used to compensate for the respective background effects beneficially in an end use application if required.

Information about the largest contribution from effects of background amplitude $\xi_j\zeta_j 2A_m B_m$ and phase $\phi_{A_m B_m \varepsilon_{m,j}}$ i.e., the interference term between the reference beam and the portion of background beam generated by the measurement beam 30A, may be obtained by measuring $S_j$ for j=1, 2, . . . , 4 as a function of relative phase shift between reference beam and the measurement beam 30A with substrate 60 removed and $A_p=0$, $p \neq m$, and Fourier analyzing the measured values of $S_j$. Such information can be used to help identify the origin of the respective background.

Other techniques may be incorporated into embodiments of the present invention to reduce and/or compensate for the effects of background beams without departing from either the scope or spirit of the present invention such as described in commonly owned U.S. Pat. No. 5,760,901 entitled "Method And Apparatus For Confocal Interference Microscopy With Background Amplitude Reduction and Compensation," U.S. Pat. No. 5,915,048 entitled "Method and Apparatus for Discrimination In-Focus Images from Out-of-Focus Light Signals from Background and Foreground Light Sources," and U.S. Pat. No. 6,480,285 B1 wherein each of the three patents are by Henry A. Hill. The contents of each of the three cited patents are herein incorporated in their entirety by reference.

The selection of values for $\xi'_j$ is based on information about coefficients $\xi_j$ for j=1, 2, . . . , 4 that may be obtained by measuring the $S_j$ for j=1, 2, . . . , 4 with only the reference beam present in the interferometer system. In certain embodiments of the present invention, this may correspond simply blocking the measurement beam components of input beam 24 and in certain other embodiments, this may correspond to simply measuring the $S_j$ for j=1, 2, . . . , 4 with substrate 60 removed. A test of the correctness of a set of values for $\xi'_j$ is the degree to which the $$\sum_{m'=1}^{2}|A'_m|^2$$

term in Equation (17) is zero.

Information about coefficients $\xi_j\eta_j$ for j=1, 2, . . . , 4 may be obtained for example by scanning an artifact past the respective eight conjugate spots corresponding to the respective eight conjugate detector pixels with one of the $A_p \neq 0$ and the remaining $A_p=0$ for p=1, 2 and measuring the conjugated quadratures component $2|A_p||C_p|\cos\phi_{A_p C_p}$ or $2|A_p||C_p|\sin\phi_{A_p C_p}$, respectively. A change in the amplitude of the $2|A_p||C_p|\cos\phi_{A_p C_p}$ or $2|A_p||C_p|\sin\phi_{A_p C_p}$ term corresponds to a variation in $\xi_j\eta_j$ as a function of j. Information about the coefficients $\xi_j\eta_j$ for j=1, 2, . . . , 4 may be used for example to monitor the stability of one or more elements of interferometer system 10.

The bi-homodyne detection method is a robust technique for the determination of conjugated quadratures of fields. First, the conjugated quadratures amplitudes $|C_1|\cos \phi_{A_1C_1}$ and $|C_1|\sin \phi_{A_1C_1}$ are the primary terms in the digitally filtered values $F_1$ (S) and $F_2$ (S) as expressed by Equations (17) since as noted in the discussion with respect to Equation (23), the terms with the factors $$\sum_{m'=1}^{2} |A'_m|^2 \text{ and } \sum_{m'=1}^{2} |B'_m|^2$$

are substantially zero.

Secondly, the coefficients of $|C_m|\cos \phi_{A_mC_m}$ and $|C_m|\sin \phi_{A_mC_m}$ terms in Equations (17) are identical. Thus highly accurate measurements of the interference terms between the return measurement beam and the reference beam with respect to amplitudes and phases, i.e., highly accurate measurements of conjugated quadratures of fields can be measured wherein first order variations in $\xi_j$ and first order errors in normalizations such as $(P_j/P'_j)$ and $(\xi_j^2/\xi_j'^2)$ enter in only second or higher order. This property translates in a significant advantage. Also, the contributions to each component of the conjugated quadratures $|C_m|\cos \phi_{A_mC_m}$ and $|C_m|\sin \phi_{A_mC_m}$ from a respective set of four electrical interference signal values have the same window function and thus are obtained as jointly determined values.

Another distinguishing feature of the bi-homodyne technique is evident in Equation (17): the coefficients of reference intensity terms $|A_m|^2$ can be made to be substantially zero by the selection of values for $\xi'_j$.

It is also evident that since the conjugated quadratures of fields are obtained jointly when using the bi-homodyne detection method, there is a significant reduction in the potential for an error in tracking phase as a result of a phase redundancy unlike the situation possible in single-homodyne detection of conjugated quadratures of fields.

The description of processing used in the single-homodyne detection of the first embodiment is the same as the description given for the bi-homodyne detection with either of the amplitudes $A_2$ or $A_1$ set equal to zero.

For the first embodiment of the present invention, the resolution represented by the high spatial frequency of the measured conjugated quadratures is $\geq \lambda/4$, e.g., $\geq 35$ nm for $\lambda=140$ nm. For a spatial resolution for the measurement of the amplitudes of the conjugated quadratures of 2.5 microns, a 1024×1024 pixel CCD, with a frame rate of approximately 100/sec, and $\lambda \geq 140$ nm, a full scan of a 300 mm wafer can made at the rate of approximately 10/hr for defects and/or artifacts with characteristic dimensions of the order of $\geq 35$ nm on either a unpatterned or patterned wafer. The defects in or on a patterned wafer are identified by comparing the measured array of conjugated quadratures with a master array of conjugated quadratures generated by a master patterned wafer that does not have any defects. The information on the master array of conjugated quadratures is stored on a memory device for access as required.

A full scan of a 300 mm wafer may be made at the rate of approximately 10/hr for defects and/or artifacts with characteristic dimensions of the order of $\geq 35$ nm for $\lambda \approx 250$ nm although the resolution represented by the high spatial frequency of the measured conjugated quadratures is $\approx 65$ nm.

The full scan of a 300 mm wafer made at the rate of approximately 10/hr for defects and/or artifacts with characteristic dimensions of the order of $\geq 35$ nm may be of the surface of the 300 mm wafer or of an internal section of the 300 mm wafer at a depth of the order of a micron.

The amplitudes and phases in an amplitude and phase representation of the conjugated quadratures measured in the first embodiment are subsequently used determine properties and locations of defects and artifacts. The properties contain information about the size and composition of the defects and artifacts. The locations determined from the phases are interferometrically determined quantities and as such possess the advantages generally assigned to measuring displacements with linear displacement interferometer.

A variant of the first embodiment comprises the same apparatus of the first embodiment except that pinhole array beam-splitter 12 is replaced with an interference type beam-splitter and a pinhole array is placed at multi-pixel detector 70. In other variants of embodiments of the present invention, pinhole array 12 is replaced by an array of microgratings such as described in cited U.S. Provisional Patent Application No. 60/459,425 (ZI-50) and U.S. patent application Ser. No. 10/816,180, (ZI-50) filed Apr. 1, 2004 and entitled "Apparatus and Method for Joint Measurement Of Fields Of Scattered/Reflected Or Transmitted Orthogonally Polarized Beams By An Object In Interferometry."

In the first embodiment, multi-pixel detector 70 may comprise a frame transfer CCD that is configured such that one set of CCD pixel signal values may be generated and subsequently stored on the CCD wafer while a frame of a second set of CCD pixel signal values may be generated before a readout of both the first and second set of the CCD signal values is made. The time required to store the first set of CCD signal values is generally much less than the time required to readout a set of CCD signal values for a frame transfer CCD. Thus, the advantage of the use of a frame transfer CCD is that the time between two consecutive pulses of input beam 20 and the corresponding time between measurements of electrical interference signal values can be much less than when using a non-frame transfer CCD.

A second embodiment of the present invention is described that comprises the interferometric confocal microscopy system of the first embodiment operated for joint measurement of conjugated quadratures using the bi-homodyne detection. In the second embodiment, beam-conditioner 22 is operated to generate beam 24 comprising two frequency-shifted components or two frequency components which reference and measurement beam components that relative phases that are shifted.

For generation of two frequency-shifted components of beam 24 when operating in the frequency shifted mode, the acoustic power to acousto-optic modulator 1120 (see FIG. 1e) is adjusted so that the intensity of diffracted beam 1122 and the intensity of non-diffracted beam 1124 are the same. The level of acoustic power in acousto-optic modulator 1120 is controlled by signal 74 generated by electronic processor and controller 80.

The remaining description of the second embodiment is the same as corresponding portions of the description given of the first embodiment of the present invention.

In other embodiments of the present invention, conjugated quadratures of a high spatial frequency component are measured with $\Lambda_y \cong \Lambda_x$ (see Equations (1) and (2)). In the other embodiments of the present invention, catadioptric imaging system 100 comprises two sections, i.e., two pie sections, of catadioptric imaging system 210 oriented 90 degrees apart about the optic axis of catadioptric imaging system 100. In addition, beam 24 is further split by a beam-splitter (not shown in a figure) to generate reference and measurement beams for the plane defined by the orientation of the second section of catadioptric imaging system 210. The remaining description of the other embodiments is the same as the description given for corresponding portions of the descriptions of the first and second embodiments. The advantage of the other embodiments is the acquisition of information about defects and/or artifacts that have characteristic dimensions of the order of $\lambda/2$ in the x and y directions simultaneously.

In another embodiment of the present invention, the height h (see FIG. 2*d*) may be adjusted to be $\approx\lambda/4$. In that case, evanescent fields will be used to detect in the high speed scan sub-wavelength defects and artifacts in or on a substrate. The remaining description of the apparatus and method of the another embodiment is the same as the corresponding portions of the description given for the first and second embodiments of the present invention.

In yet other embodiments of the present invention, information is obtained about the properties of generation and propagation of signals, e.g., electrical, thermal, or acoustical, in a section of substrate 60 by using a probe beam in addition to the measurement beam. Beam 24 comprises a probe beam that precedes the measurement beam by a time $\tau$. The probe beam and the measurement beam may have different optical wavelengths. An advantage of the use of the yet other embodiments with respect to the measurement of temporal response of the substrate is the high spatial frequency resolution in the plane of the section. The remaining description of the yet other embodiments is the same as the description given for corresponding portions of the descriptions of the first and second embodiments of the present invention.

In other embodiments of the present invention, the first and second embodiments are configured to make joint measurements of fields of orthogonally polarized beams scattered/reflected by the spots on or in substrate 60 such as described in cited U.S. Provisional Patent Application No. 60/459,425 (ZI-50) and U.S. patent application Ser. No. 10/816,180, (ZI-50) filed Apr. 1, 2004 and entitled "Apparatus and Method for Joint Measurement Of Fields Of Scattered/Reflected Or Transmitted Orthogonally Polarized Beams By An Object In Interferometry." Also in the other embodiments of the present invention, a variant of the bi-homodyne detection method is used such as described in cited U.S. Provisional Patent Application No. 60/459,425 (ZI-50) and U.S. patent application Ser. No. 10/816,180, (ZI-50) filed Apr. 1, 2004 and entitled "Apparatus and Method for Joint Measurement Of Fields Of Scattered/Reflected Or Transmitted Orthogonally Polarized Beams By An Object In Interferometry" for ellipsometric measurements.

Other embodiments are within the following claims.

What is claimed is:

1. A method of detecting defects or artifacts on or in an object, said defects or artifacts characterized by a characteristic dimension, said method comprising:
    generating an input beam for illuminating a spot at a selected location on or in the object, said spot having a size L that is substantially larger than said characteristic dimension;
    deriving a measurement beam and a reference beam from the input beam;
    directing the measurement beam onto the object as an incident measurement beam that illuminates said spot at that selected location on or in the object to produce a backscattered measurement beam;
    interfering the backscattered measurement beam with the reference beam to produce an interference beam, said reference beam being oriented relative to the backscattered measurement beam so as to produce a peak sensitivity for a portion of the backscattered measurement beam that emanates from the object at a predetermined diffraction angle;
    converting the interference beam for that selected location into an interference signal; and
    using the interference signal for that selected location to determine whether any defects or artifacts characterized by said characteristic dimension are present anywhere within a region on or in the object defined by the spot at that selected location.

2. The method of claim 1, wherein L is at least three times greater than the characteristic dimension.

3. The method of claim 1, wherein L is at least an order of magnitude larger than the characteristic dimension.

4. The method of claim 1, wherein the incident measurement beam is at an angle of incidence $\theta_I$ with respect to a direction that is normal to the surface of the object, wherein the predetermined diffraction angle is an angle $\theta_D$ relative to the direction that is normal to the surface of the object, wherein the characteristic dimension is equal to $\Lambda$, wherein the incident measurement beam is characterized by a wavelength $\lambda$, and wherein the diffraction angle $\theta_D$ is selected to satisfy the following relationship: $\Lambda[\sin(\theta_I)-\sin(\theta_D)] = \lambda$.

5. The method of claim 1, further comprising performing the steps of generating, deriving, directing, interfering, and converting for each of a sequence of different selected locations on or in the object, wherein the first-mentioned selected location is one of said plurality of different selected locations.

6. The method of claim 1, wherein generating the input beam involves generating a first beam at a first wavelength and a second beam at a second wavelength that is different from the first wavelength, said first and second beams being coextensive and sharing the same temporal window.

7. The method of claim 6, wherein generating the input beam further involves for each of a plurality of successive time intervals, introducing a corresponding different shift in a selected parameter of the first beam and introducing a different corresponding shift in the selected parameter of the second beam, wherein said selected parameters are selected from a group consisting of phase and frequency.

8. The method of claim 7, wherein using the interference signal to determine whether any defects or artifacts are present comprises:
    for each of the plurality of successive time intervals, measuring a value of the interference signal;
    from the measured values of the interference signal for the plurality of successive time internals, computing the orthogonal components of conjugated quadratures of fields of the backscattered measurement beam; and
    using the two computed orthogonal components of conjugated quadratures of fields of the backscattered measurement beam to determine whether any defects or artifacts characterized by said characteristic dimension are present within the spot.

9. The method of claim 7, wherein each of said first and second beams includes a first component and a second component that is orthogonal to the first component, wherein the selected parameter of the first beam is the phase of the second component of the first beam, and wherein the selected parameter of the second beam is the phase of the second component of the second beam.

10. The method of claim 7, wherein the selected parameter of the first beam is the frequency of the first beam, and wherein the selected parameter of the second beam is the frequency of the second beam.

11. The method of claim 7, wherein using the interference signal to determine whether any defects or artifacts are present comprises:
- for each of the plurality of successive time intervals, measuring a value of the interference signal;
- from the measured values of the interference signal for the plurality of successive time internals, computing the orthogonal components of conjugated quadratures of fields of the backscattered measurement beam; and
- using the two computed orthogonal components of conjugated quadratures of fields of the backscattered measurement beam to determine locations of any defects or artifacts characterized by said characteristic dimension within the spot.

12. The method of claim 1, wherein using the interference signal for that selected location to determine whether any defects or artifacts are present involves jointly measuring two orthogonal components of conjugated quadratures of fields of the backscattered measurement beam.

13. The method of claim 1 implemented in an inspection tool wherein the object is a mask.

14. The method of claim 1 implemented in an inspection tool wherein the object is a reticle.

15. The method of claim 1 implemented in a lithography tool wherein the object is a wafer.

16. The method of claim 1 implemented in a lithography tool wherein the object is a wafer stage and the artifacts are alignment marks.

17. The method of claim 1, wherein the input beam is characterized by a wavelength of $\lambda$ and wherein the characteristic dimension is approximately equal to $\lambda/4$.

18. A method of detecting defects or artifacts on or in an object, said defects or artifacts characterized by a characteristic dimension, said method comprising:
- focusing an incident measurement beam to a spot that illuminates a target area on or in the object to produce a backscattered measurement beam, said spot having a size L that is substantially larger than said characteristic dimension;
- interfering the backscattered measurement beam with a reference beam to produce an interference beam, said reference beam being oriented relative to the backscattered beam so as to produce a peak sensitivity for a portion of the backscattered beam that emanates from the object at a predetermined diffraction angle;
- converting the interference beam to an interference signal; and
- determining from the interference signal whether any defects or artifacts characterized by said characteristic dimension are present within the target area.

19. The method of claim 18, wherein the incident measurement beam is characterized by a wavelength of $\lambda$ and wherein the characteristic dimension is approximately equal to $\lambda/4$.

20. A method of detecting defects or artifacts on an object, said defects or artifacts being characterized by a characteristic dimension, said method comprising:
- generating a reference beam;
- generating a measurement beam for illuminating a spot on or in the object, said spot having a size L that is substantially larger than said characteristic dimension; and
- directing the measurement beam at the spot to produce a backscattered beam from the spot and interfering the backscattered beam with the reference beam to determine whether any defects or artifacts characterized by said characteristic dimension are present on or in the object.

21. The method of claim 20, wherein the measurement beam is characterized by a wavelength of $\lambda$ and wherein the characteristic dimension is approximately equal to $\lambda/4$.

* * * * *